(12) United States Patent
Barth

(10) Patent No.: US 8,952,213 B2
(45) Date of Patent: Feb. 10, 2015

(54) NEURONAL ACTIVATION IN A TRANSGENIC MODEL

(75) Inventor: Alison L. Barth, Pittsburgh, PA (US)

(73) Assignee: The Board of Trustees of the Leland Stanford Junior University, Pittsburgh, PA (US)

(*) Notice: Subject to any disclaimer, the term of this patent is extended or adjusted under 35 U.S.C. 154(b) by 211 days.

(21) Appl. No.: 10/424,164

(22) Filed: Apr. 25, 2003

(65) Prior Publication Data

US 2004/0031065 A1    Feb. 12, 2004

Related U.S. Application Data

(60) Provisional application No. 60/375,644, filed on Apr. 26, 2002.

(51) Int. Cl.
| | | |
|---|---|---|
| G01N 33/00 | (2006.01) | |
| A01K 67/027 | (2006.01) | |
| C12N 15/85 | (2006.01) | |
| C12Q 1/68 | (2006.01) | |

(52) U.S. Cl.
CPC ........ *C12N 15/8509* (2013.01); *A01K 67/0275* (2013.01); *C12Q 1/6897* (2013.01); *A01K 2217/072* (2013.01); *A01K 2227/105* (2013.01); *A01K 2267/03* (2013.01); *A01K 2267/0356* (2013.01); *A01K 2267/0393* (2013.01)
USPC ................................................ 800/3; 800/18

(58) Field of Classification Search
CPC ...................... C12N 15/8509; A01K 2227/105
USPC ...................................................... 800/3, 18
See application file for complete search history.

(56) References Cited

FOREIGN PATENT DOCUMENTS

| WO | WO 99/43783 | 9/1999 |
|---|---|---|
| WO | WO 01/36482 | 5/2001 |
| WO | WO 01/36646 | 5/2001 |
| WO | WO 01/71009 | 9/2001 |

OTHER PUBLICATIONS

Kappel CA, Regulating gene expression in transgenic animals, 1992, Current Biology, vol. 3, pp. 548-553.*
Houdebine LM, Production of pharmaceutical proteins from transgenic animals, 1994, J. of Biotechnology, vol. 34, pp. 269-287.*
Wall RJ, New gene transfer methods, 2002, Theriogenology, vol. 57, pp. 189-201.*
Cameron ER, Recent advances in transgenic technology, 197, Molecular Biotechnology, vol. 7, pp. 253-265.*
Sigmund CD, Viewpoint: are studies of genetically altered mice out of control?, Arterioscler Thromb Vasc Biol., 2000, vol. 20, pp. 1425-1429.*
Mullins JJ, Transgenesis in nonmurine species, 1993, Hypertension, vol. 22, pp. 630-633.*
Kasof GM, Kainic acid-induced neuronal death is associated with DNA damage and a unique immediate-early gene response in c-fos-lacZ transgenic rats, 1995, J. of Neuroscience, vol. 15, pp. 4238-4249.*
Yamaguchi M, Visualization of neurogenesis in the central nervous system using nestin promoter-GFP transgenic mice, 2000, Developmental Neuroscience, vol. 11, pp. 1991-1996.*
Soares Hd, Differential and prolonged expression of Fos-lacZ and Jun-lacZ in neurons, gia, and muscle following sciatic nerve damage, 2001, Experimental Neurology, vol. 167, pp. 1-14.*
Masters BR, Confocal microscopy and three-dimensional reconstruction of thick, transparent, vital tissue, 1992, Scanning Microscopy Supplement, vol. 6 pp. 71-79.*
Kovacs KJ, c-Fos as a transcription factor: a stressful review from a functional map, 1998, Neurochem. Int., vol. 33, pp. 287-297.*
Cherry SR, 2004, Physics in Medicine and Biology, vol. 49, pp. R13-R48.*
Chen et al., 2000, Learning and Memory, vol. 7, pp. 433-441.*
Soares et al., 2001, Experimental Neurology, vol. 167 pp. 1-14.*
Spergel et al., 2001, Progress in Neurobiology, vol. 63, pp. 673-683.*
Erdtmann-Vourliotis et al., 1999, Molecular Brain Res., vol. 71, pp. 313-324.*
Wilkerson et al., 2007, Cell Stress and Chaperones, vol. 12(3), pp. 283-290.*
Gammie et al., 2001, Brain Res., vol. 898, pp. 232-241.*
Schilling et al., 1991, PNAS, vol. 88, pp. 5665-5669.*
Bi et al., 2003, Biotechnol. Bioeng., vol. 81, pp. 848-854.*
Barch et al., "Anterior Cingulate and the Monitoring of Response Conflict: Evidence from an fMRI Study of Overt Verb Generation" J Cogn Neurosci 12(2):298-309 (2000).
Barth et al., "Upregulation of cAMP Response Element-Mediated Gene Expression during Experience-Dependent Plasticity in Adult Neocortex" J Neuroscience 20(11):4206-4216 (2000).
Callahan et al., "Tracing Axons" Curr. Opin. Neurobiol. 8(5):582-586 (1998).
Mombaerts et al., "Visualizing an Olfactory Sensory Map" Cell 87(4):675-686 (1996).
Rocamora et al., "Upregulation of BDNF mRNA Expression in the Barrel Cortex of Adult Mice after Sensory Stimulation" J Neuroscience 16(14):4411-4419 (1996).

(Continued)

*Primary Examiner* — Anoop Singh
*Assistant Examiner* — David A Montanari
(74) *Attorney, Agent, or Firm* — Morrison & Foerster LLP

(57) ABSTRACT

The disclosed invention provides compositions and methods for the identification of cells that are functionally activated after stimulation or during an activity while maintaining the viability of the identified cells.

34 Claims, 13 Drawing Sheets

(56) References Cited

OTHER PUBLICATIONS

Staiger et al., "Exploration of a Novel Environment Leads to the Expression of Inducible Transcription Factors in Barrel-Related Columns" Neuroscience 99(1):7-16 (2000).

Staiger et al., "Excitatory and Inhibitory Neurons Express c-Fos in Barrel-Related Columns after Exploration of a Novel Environment" Neuroscience 109(4):687-99 (2002).

Thomas, M. J. et al., "Long-Term Depression in the Nucleus Accumbens: A Neural Correlate of Behavioral Sensitization to Cocaine" Nat Neurosci 4(12):1217-23 (2001).

Yamaguchi, M. et al., "Visualization of Neurogenesis in the Central Nervous System Using Nestin Promoter-GFP Transgenic Mice" NeuroReport 11(9):1991-1996 (2000).

Feng et al., Neuron (2000) 28:41-51.

Keller-Peck et al., Neuron (2001) 31:381-394.

Svoboda et al., Nature (1997) 385:161-165.

Svoboda et al., Nat. Neurosci. (1999) 2:65-73.

Helmchen et al., Nat. Neurosci. (1999) 2:989-996.

Charpak et al., PNAS USA (2001) 98:1230-1234.

Chen et al., Learn. Mem. (2000) 7:433-441.

\* cited by examiner

Figure 3 Barrel cortex after exploratory behavior, living tissue

Figure 4 Hypotonic saline injection, 4 hrs post injection, living tissue

Barrel cortex

Olfactory bulb

Figure 8 C1 whisker only, layer IV barrel cortex, fixed and flattened tissue

NEURONAL ACTIVATION IN A TRANSGENIC MODEL

RELATED APPLICATIONS

This application claims benefit of priority from U.S. Provisional Application 60/375,644, filed 26 Apr. 2002, which is hereby incorporated in its entirety as if fully set forth.

TECHNICAL FIELD

The present invention relates to compositions and methods for identifying, from a population of cells, cells that are functionally activated. The invention utilizes a nucleic acid encoded reporter, the expression of which undergoes a detectable change in cells that are functionally activated in response to a stimulus, or as part of an activity, at the cell, tissue, organ, or organism level. Detection of the change identifies individual cells as activated by a stimulus or during an activity and thus as members of a functional subset of the total cells in a population. Advantageously, the identified cells remain viable for further study or characterization. In one embodiment, the invention provides for the identification of neurons that are functionally activated by a stimulus or during an activity involving brain function.

BACKGROUND ART

A multicellular organism is composed of individual cells that are organized structurally and functionally into tissues, organs, and systems to conduct various activities of the organism. For example, muscle cells have been recognized as functionally involved in movement while liver cells have been identified as removing toxic substances. There remain many instances, however, where it is difficult to identify the individual cells involved in a particular activity or to identify subsets of cells and their different roles during a complex activity. The inability to identify individual cells, as opposed to a region of cells, as involved in various brain functions is one example of the continuing difficulties in the field.

The central nervous system of mammals is composed of millions of neurons that are connected to each other in a wide variety of highly specific combinations. Individual neurons have distinct developmental programs, different patterns of connectivity with other neurons, and restricted anatomical locations. To complicate things further, neurons alter their functional properties in an experience-dependent way. The key determinants of a given neuron, such as its functional properties and it connections to other cells, thus change over time and in response to various stimuli.

In order to determine the neural basis for behavior and memory, scientists have employed a variety of techniques to allow the identification of brain areas, and thus particular neurons, that may be involved. For example, tissue lesion, either by stroke, surgery or toxin exposure, has been used to verify the involvement of a region of the central nervous system (CNS) in a particular behavioral task or response. This has been a fruitful method in some respects, as it has allowed identification of the hippocampus, for example, as a site of short-term memory storage, the hypothalamus as an area involved in appetite and thirst regulation, and the cerebellum as an area involved in motor planning and coordination. Lesion analysis has not provided a direct test of functional involvement, however, and usually involves the disruption of an enormous number of neurons without identification of which neurons are actually involved in a particular behavior. Many of the neurons in an identified CNS region may not be involved in the behavior being assayed.

In a similar attempt to uncover the neural basis of memory and behavior, studies have attempted to use assays of single neurons in vivo in an attempt to look for changes in neuronal firing properties after training or during a particular behavioral state. (Thomas M J, Beurrier C, Bonci A, Malenka R C. Long-term depression in the nucleus accumbens: a neural correlate of behavioral sensitization to cocaine. Nat Neurosci. 2001 December; 4(12):1217-23.) This technology is limited, however, in that it is difficult to distinguish the activated subset of neurons (signal) that are directly involved in a behavior from those that are not (noise). For this reason, sophisticated statistics and large data sets are required to detect any changes between trained and untrained animals, for example.

In another study, a genetic approach was used to visualize axons from a subset of olfactory sensory neurons as they project to the olfactory bulb (Mombaerts et al. Cell 87(4): 675-686, 1996). Additional projections of neurons have been charted by the use of a variety of axon-tracing techniques (Callahan et al. Curr. Opin. Neurobiol. 8(5):582-586, 1998).

Citation of documents herein is not intended as an admission that any is pertinent prior art. All statements as to the date or representation as to the contents of these documents is based on the information available to the applicant and does not constitute any admission as to the correctness of the dates or contents of these documents.

DISCLOSURE OF THE INVENTION

The present invention provides compositions and methods for identifying one or more cells as functionally activated in response to a stimulus, or as involved in an activity, at a cell, tissue, organ, or organism level. The invention may be used to identify individual, or one or more subsets of, cells within a population as functionally heterogeneous from other cells even though the population has been characterized as homogenous or heterogeneous by other criteria. Functionally heterogeneous cells may be considered as belonging to different subsets within the larger population from which they are identified. The ability of the invention to identify functional heterogeneity within a cell population is particularly advantageous where a large number of cells have been recognized as playing a role (or being capable of being activated) in a particular response or activity of an organism, but it is unclear as to the individual cells that are functionally involved in the response or activity.

In one aspect of the invention, a stimulus is utilized to activate one or more cells of an organism. The stimulus may be of any type or form as long as it activates one or more cells of a larger set of cells via a unique molecular or structural characteristic. Stated differently, the stimulus induces activity in one or more cells of an organism by interaction with a molecular, structural, or anatomical feature of the cell. In one set of preferred embodiments of the invention, administration of a drug or other chemical compound is used as the stimulus for activation of cells. Interaction between the drug or chemical compound and its cellular target, found only in a subset of cells, activates said cells. The present invention provides a means by which those activated cells are differentially identified while retaining cell viability. Examples of molecular targets that mediate cell activation include cell surface receptors and structural molecules (including components of the major histocompatibility complex), intracellular receptors, enzymatic proteins, non-enzymatic proteins, and nucleic acids.

While the present invention may be practiced with use of a stimulus for which the cellular target is known, the invention may also be advantageously practiced with a stimulus for which the target is not known. This permits the identification of the cell(s) activated by a particular stimulus, such as drug or other chemical compound, without the need for knowledge concerning its mechanism of action. As a non-limiting example, a chemical compound may activate certain cells of an organism after in vivo processing into a different form. The chemical compound may thus be considered a "prodrug" where the processed form of the compound interacts with a cellular target to activate cells. The present invention permits the identification of the activated cell(s) without the need to know the nature of the processed form of the compound.

As used herein, functional activation refers to the induction of a change in a cell such that it changes one or more of its cellular processes as compared to before activation and/or begins a cellular process that was not conducted before activation. Stated differently, a functionally activated cell has a change in cell physiology compared to its physiology before activation. Non-limiting examples of such a change include activation of a second messenger cascade to effect a change in cell function; activation of expression of a gene; entry into the cell cycle; secretion of a protein, fusion of cellular vesicles, or induction of apoptosis.

To detect functionally activated cells, the present invention provides a nucleic acid construct comprising regulatory sequence(s) operably linked to a sequence encoding a detectable reporter (or marker). The regulatory sequence(s) control expression of the reporter such that its expression undergoes a detectable change in cells that are functionally activated in response to a stimulus or as part of an activity. The regulatory sequence(s) may be directly or indirectly responsive to the stimulus, and is/are preferably endogenously present in cells that become activated in response to the stimulus or during the activity. Where the regulatory sequence(s) are naturally occurring, all or part of the coding region normally controlled by the regulatory sequence(s) may remain present in the construct as long as the reporter may be expressed in a detectable form while maintaining cell viability. Alternatively, the coding region normally controlled by the regulatory sequence(s) may be mutated to result in an inactive product without affecting the expression or detectability of the reporter. The nucleic acid construct is introduced into the cells of a population either directly or by introduction into one or more totipotent, multipotent, or pluripotent progenitor or precursor (e.g. stem) cells.

A detectable change in expression controlled by the regulatory sequence(s) may be via transient, or more prolonged, induction of the regulatory sequence(s). The detection of changes due to transient induction may be improved by the use of a reporter that is stably expressed (e.g. not readily degraded or masked) such that upon transient induction, expression of the reporter is increased and remains detectable even after the induction has ended. The present invention advantageously provides for the use of reporters which are detectable without requiring the killing of the cell(s) into which the reporter is expressed.

The invention also provides for introduction of the construct into cells by means known in the art to produce cells, in vitro or of an organism, containing said construct for use in the practice of the invention. Introduction of the vector may thus be by techniques such as, but not limited to, (viral or non-viral) vector mediated, "knock in" recombination, electroporation, liposome mediated, and direct injection. In one aspect of the invention, the construct is used to produce a transgenic non-human animal comprising cells that contain the construct. Such a transgenic animal may be used to identified functionally activated cells in response to a stimulus or as part of an activity. In another aspect, tissue or organ material (e.g. tissue or organ slices) may be isolated from such a transgenic animal and used in vitro to identified functionally activated cells. In a further aspect of the invention, the construct is introduced into a population of cells in culture such that they may be used in vitro to identify cells that are responsive to a stimulus.

After identification of functionally activated cells as provided by the present invention, the identified cells may be further characterized. Such characterization may be of the cells in situ (within an animal), or after isolation (such as, but not limited to, removal of a tissue section or slice or isolation of individual cells). Non-limiting examples of further characterization include gene expression, cell growth, response to a chemical or drug agent, secretion of proteins, changes in morphology or mobility/invasiveness and/or other assays for changes in cellular physiology. Where the activated cells are neurons, non-limiting examples of further characterization include changes in dendritic outgrowth, remodeling of the numbers and/or positions of axons, modification of synaptic function, and electrophysiology.

The present invention provides, in one embodiment, a novel means of identifying neurons involved in brain activity/function. Neurons that are functionally activated by a stimulus, or during an activity, are identified by detecting of the expression of a reporter by a construct of the invention wherein the regulatory sequence(s), operably liked to a sequence encoding the reporter, are induced directly or indirectly by said stimulus or during said activity. Individual, or subsets of, neurons that respond to a physical (e.g. electrical) or chemical stimulus may be identified and isolated from other neurons not involved in a response to a stimulus. The identified neuron(s) may be physically separated from other neurons or used in situ to further characterize the neuron(s) and their involvement in brain function. Axon-tracing techniques may also be used to chart the projections of the identified neurons. The invention advantageously permits identification of the neuron(s) while leaving them alive for further characterization(s).

The regulatory sequence(s) operably linked to control expression of the reporter may be directly or indirectly responsive to the stimulus, and is/are preferably endogenously present in neurons that are functionally activated in response to a stimulus or during an activity. In one embodiment of the invention, a construct containing a reporter (or marker) operably linked to regulatory sequence(s) is introduced into one or more neuron(s) of an animal. In another embodiment, the construct is introduced into one or more neuron(s) in vitro, such as in cultured cells or cells isolated from an animal. Of course multiple copies of the construct may be introduced into each cell. In preferred embodiments of the invention, the construct is introduced into a cell, blastocyst, or embryo of a non-human animal capable of developing into a mature animal to produce a transgenic organism. Preferably all, or nearly all, of the transgenic animal's neurons contain the combination of the reporter operably linked to the regulatory sequence(s) in an expressible manner.

Regulatory sequences that may be used in the practice of the invention include any that are activated in response to stimulation of a neuron or those that are preferentially expressed during an activity. Preferably, the sequences are those that display low levels of, or no detectable, expression in the absence of stimulation or activity. Preferred regulatory sequences are those that activate transcription in response to stimulation by touch (tactile), sound (auditory), sight (visual), taste, smell (olfactory), thirst, and hunger. Additional regulatory sequences that may be used in the practice of the invention are those activated in response to learning or involved in neuronal plasticity, gain of function, or attenuation of function. In a particularly preferred embodiment of the invention, and based upon the long-standing observation that the immediate-early gene c-fos is expressed by individual neurons in a regionally specific manner after a stimulus, the invention provides a nucleic acid construct containing the c-fos gene coupled to a green fluorescent protein (GFP) coding region. This construct thus expresses the non-toxic fluorescent GFP reporter under the control of the regulatory sequences of the c-fos gene.

The invention also provides for the preparation and use of nucleic acid constructs to prepare cells and transgenic plants and non-human animals for use in the methods of the invention. The invention may also be used in certain applications in human beings. Preferred non-human animals for the practice of the invention are mammals, particularly those important to agricultural applications (such as, but not limited to, cattle, sheep, horses, and other "farm animals") and for human companionship (such as, but not limited to, dogs and cats). In an alternative embodiment of the invention, the non-human animals may be those that are particular advantageous for research purposes, such as mice, rabbits, rats and non-human primates. The cells and transgenic plants and animals of the invention may optionally comprise multiple nucleic acid constructs to permit the identification of multiple functional activation events in the same cell(s) or in the same tissue or organism.

In an embodiment of the invention for further characterization of identified neurons, whole-cell recording techniques may be used to allow identification of individual neurons that are functionally activated following a given stimulus or learning event, as well as detailed analysis of the types of changes in this subset of cells that accompany learning. The present invention provides the ability to determine the neural basis of behavioral states and learning and memory by assaying function in living brain cells. An important benefit provided by the present invention is that it would allow functional characterization of cellular subtypes involved in pathological states, as well as the ability to directly examine drug efficacy against an identified target population of cells using whole-cell recording techniques or other assays of cell function.

The invention further provides for the ability to identify chemical agents as functionally activating cells that are activated as part of a naturally occurring response. As a non-limiting example, the invention provides methods for comparing the neurons activated due to a feeling of fullness in comparison to neurons activated upon administration of an appetite suppressant to determine whether the same neurons are functionally activated.

BRIEF DESCRIPTION OF THE DRAWINGS

FIG. 9, panel A: expression of fosGFP in the barrel cortex of normal (unplucked) animals is low (line 1-3 shown; control, unplucked hemisphere is from same animal as in panel B). FIG. 9, panel B: fosGFP expression in the spared barrel after unilaterally plucking all but a single large facial vibrissa, whisker D1, for 24 hrs. Arrow indicates spared barrel column. FIG. 9, panels C and D: fosGFP expression is induced in the PVN after dehydration (panel D) but not in control, PBS-injected animals (panel C; line 6-1 shown). FIG. 9, panels E-H: compared to control, PBS-injected animals (panel E), clozapine stimulates increased fosGFP expression in the striatum (panel F). Increased fosGFP expression after clozapine injection was also observed in the nucleus accumbens (panel H) compared to control, PBS injected animals (panel G; line 5-1 shown). Bar=100 μm. Abbreviations: 3v=$3^{rd}$ ventricle, lv=lateral ventricle, cc=corpus callosum, ac=anterior commissure.

FIG. 10, panel A shows a low magnification view of the barrel cortex, showing a single medial barrel that corresponds to the D1 whisker (arrow) showing strong GFP fluorescence. Some areas of the brain show intrinsic fluorescence, such as areas of the hippocampus. Bar for FIG. 10, panels A and B=200 μm. FIG. 10, panel B shows adjacent brain slice showing the lateral edge of the barrelfield, where unplucked whiskers corresponding to the small facial vibrissae project. Fos-GFP expression was also strong in this sensory-spared region (between arrowheads). FIG. 10, panel C shows high magnification view of panel A, with layer IV of the spared barrel in focus. Note the sharp edges delineated by fosGFP expression, corresponding to the margins of the spared barrel. Bar for FIG. 10, panels C and D=100 μm. FIG. 10, panel D shows high magnification view of panel A, with layer II/III of the spared barrel in focus. Cells are more sparsely labeled than in layer IV, but fosGFP signal was brighter amongst this group of labeled cells.

MODES OF CARRYING OUT THE INVENTION

Figure 1:
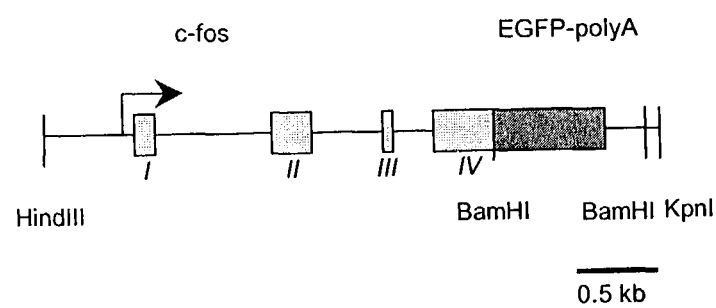
FIG. 1: Insertion of the c-fos gene in frame into the coding sequence for EGFP from Clontech into the BamHI site, and contained the polyA signal from the commercial construct.

The invention provides methods for the identification of one or more cells of a population as functionally activated in response to a stimulus or as part of an activity at a cell, tissue, organ, or organism level. The methods may be practiced with cells in an animal, cells in a tissue or organ sample, or cells in vitro, such as cells in culture. In one embodiment, the methods are practiced with a non-human animal to identify cells activated in response to stimulation of, or activity by, the animal. In one set of preferred embodiments, the invention is practiced to identify differentiated cells (as opposed to totipotent, pluripotent, multipotent or progenitor cells) as functionally activated.

Stimulation (or stimulus or stimuli) as used herein refers to the application or withholding of an agent or action that induces organic activity or a response in a living cell or animal. The terms also includes the neurophysiological definition of application of an agent or action to a responsive structure, such as neurons or a central nervous system, even if the strength of the stimulus induces no response. The term may also be defined as an agent or action which results in a change in neuronal gene expression or a neuronal response, the latter of which includes changes in connections with other neurons as a non-limiting example.

Generally, a stimulus may be physical or chemical and includes behavioral, physiological, and pharmacological stimuli. Non-limiting examples include administration of a (test) drug, pain, or pleasure; induction of dendritic outgrowth; learning; fear; sensory deprivation or stimulation; stress; reward for behavior that they attend to; conditioning; visual, audio, location or olfactory cues; administration of a mind altering drug selected from marijuana, cocaine, heroin, alcohol, or functional equivalents thereof; psychotropic agent (e.g. LSD, haloperidol, Prozac™, olzapine, olanzapine, clozapine, lithium, and Exctasy); mating; aggression; sexual behavior; maternal behavior; social dominance; deprivation of water or food; a wound or injury; response to a growth factor or cytokine or endocrine or paracrine; and transplantation of foreign cells or tissue. Non-limiting examples of learning include increasing memory and mazes, such as an elevated plus maze, a light/dark box, an open field test, and a water maze. Non-limiting examples of cues include images, sounds, and smells as well as any cue that is linked to drug addition so that cells that are functionally activated by administration of a drug (such as, but not limited to nicotine, marijuana, caffeine, cocaine, heroin, and alcohol) may be compared to cells that are functionally activated by cues associated with the effects of the drug. Particularly preferred is the use of sensory stimulation, hypothalamic activation, or (antipsychotic) drug adminstration. In embodiments of the invention relating to neurons, nerve impulses or electrical activity may also be a stimulus.

As used herein, an "activity" at a cell, tissue, organ or organism level refers to acts conducted by living cells, tissues, organs or organisms that are not responsive to a stimulus. At the organism level, an activity is often a behavior that is performed by an animal without being a response to an external stimulus. Non-limiting examples include exploratory behavior; sleep and stages thereof; narcolepsy (stimulation with orexin may also practice with the present invention); lactation; parturition (stimulation with oxytocin may also be practice with the present invention); and movement (e.g. motor control, motor training, paw reach, lever pressing, and progress through a maze). At the tissue or organ level, an activity is often the result of biochemical activity of the tissue or organ or the cells therein which functionally activates other cells. Non-limiting examples include the secretion of signaling molecule or a paracrine or endocrine which activates other cells in a tissue or organ.

The methods of the invention may also be practiced with cells of a tissue or organ sample, such as a tissue section or slice to identify cells activated in response to a stimulus or during an activity. One non-limiting example is identification of cells in a brain slice that are functionally activated in response to administration of a drug or electrical excitation of one or more neurons. Another non-limiting example is identification of cells in a blood sample that are functionally activated in response to administration of a drug or foreign agent or cell. Electrical stimulation may also be practice in situ within an animal.

In another embodiment, the methods of the invention may be practiced with cells in vitro to identify cells that are functionally activated in response to a stimulus. Examples of such methods include, but are not limited to, screening candidate drug compounds for the ability to functionally activate said cells, screening candidate drug compounds for the ability to modulate (increase or decrease) functional activation of cells by an activating stimulus, and identifying subsets of cells activated by administration of a drug compound.

The present invention may be advantageously used in combination with techniques for general identification of cells involved in a particular response or activity. In the case of the brain, techniques that generally identify cells associated with a particular brain function include computerized axial tomography (CAT), magnetic resonance imaging (MRI) and positron emission tomograph (PET), none of which have resolutions capable of identifying individual cells. As a non-limiting example, cells that have been identified as being in a brain location responsible for a particular response or activity are a cell population which may be used in the practice of the invention to identify particular cells that are functionally activated in the response or activity. These identified cells constitute a functional subset of the larger population. These functional subsets are of particular interest for further studies of the response or activity.

The present invention provides for the identification of functionally activated cells while maintaining the viability of the identified cells as well as neighboring cells or other cells in the same tissue. Cell viability is maintained by the use of a reporter the detection of which does not require cell death. Preferred reporters of the invention are luminescent or fluorescent proteins that are non-toxic or minimally toxic when expressed in cells. Non-limiting examples include green fluorescent protein (GFP), modified or enhanced green fluorescent protein (EGFP as used in the following examples), yellow fluorescent protein (YFP) and enhanced YFP (EYFP), cyan FP, blue FP, red FP, luciferase, or analogs thereof. See U.S. Pat. Nos. 5,958,713, 5,683,888, 5,491,084 and 5,804,387, all of which are incorporated herein as if fully set forth. HcRed, a far-red fluorescent protein generated by site-directed and random mutagenesis of a nonfluorescent chromaprotein isolated from the reef coral *Heteractis crispa*, may also be used, especially in multiplex with other fluorescent proteins because of its fluorescence in the far-red region of the spectrum. The invention may also be practiced with any of the reporters described herein that is encoded by a nuclei acid sequence which has been codon optimized for the cells in which the reporter will be used.

The invention may also be practiced with various forms of GFP that exhibit colors other than green. Additionally, GFP isolated from sources other than the jellyfish *Aequorea Victoria*, such as the sea pansy *Renilla reriformis*, may be used. As non-limiting examples, the GFPs with GenBank accession numbers U47949 (AGP1); U43284; U36202; U36201; U19282; U19279; U19277; U19276; U19281; U19280; U19278; L29345 (*Aequorea victoria*); M62654 (*Aequorea victoria*); and M62653 (*Aequorea Victoria*) may be used. Alternatively, modified GFPs such as AF007834 (GFPuv); U73901 (*Aequorea victoria* mutant 3); U50963 (Synthetic); U70495 (soluble-modified green fluorescent protein (smGFP)); U57609 (enhanced green fluorescent protein gene); U57608 (enhanced green fluorescent protein gene); U57607 (enhanced green fluorescent protein gene); U57606 (enhanced green fluorescent protein gene); U55763 (enhanced green fluorescent protein (egfp); U55762 (enhanced green fluorescent protein (egfp); and U55761 (enhanced green fluorescent protein (egfp) may be used. GFPs from microorganisms such as U89686 (*Saccharomyces cerevisiae* synthetic green fluorescent protein (cox3::GFPm-3) gene); and U89685 (*Saccharomyces cerevisiae* synthetic green fluorescent protein (cox3::GFPm) gene) may also be used in the present invention. Synthetic GFPs such as U87974 (Synthetic construct modified green fluorescent protein GFP5-ER (mgfp5-ER)); U87973 (Synthetic construct modified green fluorescent protein GFP5 (mgfp5)); U87625 (Synthetic construct modified green fluorescent protein GFP-ER (mfgp4-ER)); U87624 (Synthetic construct green fluorescent protein (mgfp4) mRNA)); U54 830 (Synthetic *E. coli* Tn3-derived transposon green fluorescent protein (GF); AAB47853 ((U87625) synthetic construct modified green fluorescent protein (GFP-ER)); and AAB4785 2 ((U8762 4) synthetic construct green fluorescent protein) may also be used. Nucleic acids encoding blue fluorescent proteins and identified by the following GenBank accession Nos. may be used: U70497 (soluble-modified blue fluorescent protein (smBFP); 1BFP (blue variant of green fluorescent protein); and AAB 16959 (soluble-modified blue fluorescent protein). Similarly, nucleic acids encoding red fluorescent proteins identified by the following GenBank accession Nos. may be used: U70496 (soluble-modified red-shifted green fluorescent protein (smRSGFP); and AAB16958 (U70496) soluble-modified red-shifted green fluorescent protein). Additionally, a fluorophore that changes color with time may be used in the present invention to provide the ability to follow expression over time or determine the approximate time point at which expression occurred. See Teiskikh et al. (*Science* 290:1585-1588, 2000) for an example of such a fluorophore.

Fluorescent proteins, or fluorophores in general, are particularly preferred in the practice of the invention because they are auto-fluorescent and do require other substrates or co-factors for its fluorescence. This is in contrast to the use of reporters that require fixation (and thus death) of cells before they may be detected. See Crossin et al. (WO 99/43783), Smeyne et al. (Neuron 8(1):13-23, 1992), and Wilson et al. (Proc. Nat'l. Acad. Sci, USA 99(5):3252-3257, 2002), all of which are incorporated herein as if fully set forth.

Nucleic acid molecules encoding reporters of the invention may be operably linked to one or more regulatory sequences to form nucleic acid constructs of the invention. As used herein, the term "operably linked" refers to a functional linkage between the regulatory sequence(s), which comprise at least a promoter, and a coding sequence the expression of which is under the control of the regulatory sequence(s). The term "regulatory sequence" refers to nucleic acid sequences in cis which act independently or are bound by transcription factors, regulatory proteins and components of the transcription machinery (such as RNA polymerase) to transcribe a nucleic acid sequence. The term is used to refer to promoter sequences, transcription binding sites, enhancers, repressor binding sites, and other cis acting sequences that regulate transcription. In preferred embodiments of the invention, eukaryotic regulatory sequences are used in the practice of the invention, with those of an endogenous gene that is activated in response to a stimulus or during an activity being particularly preferred.

As used herein, a "gene" is a polynucleotide that is capable of expressing a discrete product, whether RNA or proteinaceous in nature. It is appreciated that more than one polynucleotide may be capable of encoding a discrete product. The term includes alleles and polymorphisms of a gene that encodes the same product, or a functionally associated (including gain, loss, or modulation of function) analog thereof, based upon chromosomal location and ability to recombine during normal mitosis. The term also includes the regulatory sequence(s) that are operably linked to a polynucleotide sequence that is transcribed to express an RNA or proteinaceous product. Regulatory sequences, including the promoter region and other regulatory regions, are often at the region 5' to the coding sequence, but may also be found in introns and coding regions, as well as the 3' untranslated region. Regulatory sequences of genes that are not activated by a stimulus or during an activity or expressed mainly during particular developmental stages (such as that of the nestin or N-cam genes) are preferably not used in the practice of the invention.

While the invention may be practiced with less than all of a eukaryotic gene's regulatory sequences, all of the regulatory sequences as well as all or part of the transcribed sequences are preferably used to control expression of a reporter encoding sequence. Use of all of a gene's regulatory sequences as well as the transcribed sequences increases the likelihood that the nucleic acid constructs of the invention will be regulated in a manner similar or identical to the endogenous gene. Non-identity of regulation may be due to differences in position effects and/or chromatin structure between the endogenous gene and the constructs of the invention. The constructs of the invention may simply be fusions of the endogenous gene sequences with a reporter encoding sequences such that a fusion protein is produced upon transcription and translation of the construct. The detectability of the reporter in such a fusion molecule may be confirmed in vitro before use of the constructs in the practice of the invention.

In one set of preferred embodiments of the invention, the regulatory sequences of cellular immediate early (cIE) genes are used to control expression of a reporter in the practice of the invention. The cIE genes have been observed to be induced, sometimes transiently, by a variety of stimuli. Non-limiting examples of such genes include c-fos (including fosB), c-jun (including junB), JunD, zif268, krox24, ngfi-A, egr-1, krox20, egr-2, and egr-3. In another set of preferred embodiments, the regulatory sequences of genes responsive to changes in intracellular Ca++ levels, PKA signaling, cAMP signaling, CAMKIV signaling, and MAPK signaling are used to control expression of a reporter. In a further set of embodiments, the regulatory sequences of genes involved in synaptic function, such as but not limited to narp, arc/Arg 3.1, beta-activin, homer, and cpg-15/neuritin may be used to control expression of a reporter. In an alternative set of preferred embodiments, the regulatory sequences of genes activated after some patterns of neuronal activity, such as but not limited to, tyrosine hydroxylase, cox-2, nur77, nurr1, neuronal nitric oxide synthase, brain-derived neurotrophic factor (BDNF), IGF-1, NGFI-B, and trkB may be used to control expression of a reporter. An example of using less than all of a gene's regulatory sequences is found in the case of cpg15, where the promoter is approximately 7 kb in length (without the coding sequence) but a 1.9 kb fragment may be used in the practice of the invention. Moreover, constructed transgenes containing multiple CRE binding sites may also be used to control reporter expression. Other genes for use in the present invention include prostaglandin endoperoxide H synthase-2 (PGHS-2), heat shock protein (HSP) 70, and HSP 72.

While the regulatory sequences of the above genes may be most advantageously applied to the identification of functionally activated neuronal cells, they may also be used in applications of the invention to identify functionally activated cells in general, because expression of these genes is not necessarily limited to neuronal cells. Preferably, however, a gene that display a dominant negative effect due to dimerization or multimerization of its gene product (alone or with other gene products) may be selectively not used in the practice of the present invention where a construct encoding a fusion protein of the gene product and a reporter is used because the fusion protein may cause a dominant negative effect in cells despite expression of the endogenous gene.

Additional genes, and their regulatory regions, which may be used in the present invention are readily identified by a simple screen to identify gene activation in response to a stimulus or during an activity. For example, a comparison of gene expression in cells exposed to a stimulus or undergoing an activity with genes expression in control cells that are not so exposed or active permits the readily identification of genes the expression of which are activated by said stimulus or during said activity. This comparison may be made by use of cells in general, such as that of a brain section or slice, without isolation of the particular cells in which gene expression was activated. The regulatory regions of these genes can then be used to control expression of a reporter such that cells that are functionally activated by said stimulus or activity may be identified via the present invention.

The use of the regulatory sequence(s) of an endogenous gene that is activated in response to a stimulus or during an activity permits expression of the reporter to undergo a change upon activation. Thus regulatory sequence(s) that basally express a reporter (such as those of the AP-1 complex or c-fos) may still be used in the practice of the invention so long as they undergo activation to result in a detectable change in reporter expression. Additionally, the present invention is preferably practiced with a reporter that detectable for a number of hours after expression. This has been confirmed in the case of the GFP reporter as described in Example 1 herein.

The present invention also provides for the use of more than one nucleic acid construct in combination to identify cells that are functionally activated by more than one stimulus or during more than one activity. A first nucleic acid construct comprising a first regulatory sequence operably linked to a first reporter may be used in combination with a second nucleic acid construct comprising a second regulatory sequence operably linked to a second reporter where the regulatory sequences of each construct are distinct and the reporters of each construct are distinct. Thus the present invention may be practiced in a multiplex format where activation of two regulatory sequences may be detected by assaying for the two different reporters in the same cell, tissue, organ, or animal. Of course more than two nucleic acid constructs may be used together.

The nucleic acid constructs of the invention may be introduced into cells by means known in the art, including direct introduction or introduction into one or more totipotent, multipotent, or pluripotent progenitor or precursor (e.g. stem) cells. In preferred embodiments of the invention, a construct is introduced by techniques such as, but not limited to, (viral or non-viral) vector mediated, "knock in" recombination, electroporation, and direct injection.

Non-limiting examples of viral vectors include parvoviral, paramyxoviral, adenoviral and lentiviral (e.g. retroviral) vectors known in the art. Hybrid vectors may also be used. Viral vectors may be used to selectively deliver nucleic acid constructs of the invention to particular cells, tissues or organs of an animal without the need for preparation of a transgenic animal.

Generally, the introduction of a nucleic acid construct may occur with stable integration into the cell's genome. Alternatively, the construct may be maintained episomally. Expression from a stably integrated construct is under the control of cellular influences as they affect the regulatory sequence(s) of the construct. In the case of introduction by "knock in" recombination, the reporter encoding sequence is targeted to a desired endogenous gene and inserted using position specific techniques such as homologous recombination. The "knock in" may be such that all or part of the coding sequence of the endogenous gene is lost (such that the endogenous regulatory sequences control expression of the reporter and not the endogenous coding sequence), but preferably, some or all of the endogenous coding sequence is maintained and used to produce a fusion sequence capable of expressing the reporter as a fusion protein.

In one preferred embodiment of the invention, the construct is used to produce a transgenic non-human animal comprising cells that contain the construct. This may be accomplished by methods known in the art, such as introduction of nucleic acid molecules into a fertilized egg, an embryo, or a blastocyst followed by implantation in an animal for gestation followed by birth. Transgenic animals may be confirmed as containing a nucleic acid construct of the invention by a variety of methods, including sampling of cells for the presence of the reporter or sequences encoding all or part of it and/or detecting expression of the reporter in the animal. See Enikolopov et al. (WO 01/36482) and Yang et al. (WO 01/71009). The invention also contemplates use of the progeny of such transgenic animals as long as the progeny retains a construct of the invention. Alternatively, the nucleic acid constructs of the invention may be introduced into cells of an animal while in utero.

Such transgenic animals are preferably used to identify functional activation of cells in response to a stimulus or as part of an activity at the organism level. The transgenic animals may also be used as a source of tissue or organ material (e.g. tissue or organ sections or slices) for use in the practice of the invention. As non-limiting examples, sections or slices of the brain that have been identified as involved in particular activities may be used as tissues in the practice of the invention. Exemplary brain tissues include those from the primary sensory cortex and associated areas, activated by altered sensory (visual, auditory, somatosensory) experience; the motor cortex, activated by behavioral training-motor task; the anterior cingulate cortex, activated by attention; the piriform cortex, activated by olfactory stimuli; the hippocampus and neocortex, involved in declarative and procedural memory tasks; the hippocampus, involved in spatial learning and odorant discrimination; the hypothalamus, involved in appetite (including hunger and satiety stimuli); the amygdala, involved in fear conditioning and odorant discrimination; the neocortex, activated by injury, ischemia, and stroke; the olfactory bulb, activated by odorant exposure and involved in olfactory learning; the accessory olfactory bulb, activated by pheromone exposure; the hippocampus, neocortex, piriform cortex, amygdala, hypothalamus, and dentate gyrus, activated by generalized seizures and kindled seizures; the trigeminal nucleus, activated by axotomy and electrical stimulation; the nucleus accumbens, ventral tegmental area, and striatum, involved in addiction (drugs of abuse) and activated by antipsychotic drug administration; the spinal cord, thalamus, periaqueductal grey, and reticular nucleus, activated by pain; the retina, suprachiasmatic nuclei, and lateral geniculate nucleus, activated by light stimulation/circadian rhythms; the locus coerulus and hypothalamus, involved in sleep; the paraventricular, supraoptic nuclei of the hypothalamus, central nucleus of the amygdala, bed nucleus of the stria terminalis, dorsal vagal complex, and area postrema, activated by nauseogenic treatment; the hypothalamic paraventricular nucleus and central nucleus of the amygdala, activated by physiological stressors such as haemorrhage and immune challenge; the hypothalamic paraventricular nucleus and medial nucleus of the amygdala; activated by psychological stressors such as noise, restraint, and forced swim; the claustrum, bed nucleus of the stria terminalis, medial preoptic nucleus, paraventricular nucleus, medial amygdala, and cortical amygdala, involved in maternal aggression; the olfactory bulb, cingulate cortex, hippocampus, entire hypothalamus, septal nuclei, and amygdaloid complex, involved in/activated by defeat stress (interspecific aggression); the posterodorsal preoptic nucleus, subparafascicular thalamus, posterodorsal medial amygdale, bed nucleus of the stria terminalis, ventrolateral hypothalamus, and neocortex, activated by sex; the medial amygdaloid nucleus, ventrolateral hypothalamus, bed nucleus of the stria terminalis, and midbrain central gray, activated by male aggression; the trigeminal nucleus caudalis, area postrema, nucleus of the solitary tract, parvicellular reticular nucleus, locus coeruleus, parabrachial nucleus, and raphe nuclei, activated by migraine/noxious trigeminal stimulation; the cochlear nucleus complex, superior olivary complex, inferior colliculus, auditory cortex and associated areas, activated by auditory stimuli; the hippocampus and CNS in general, involved in apotosis and neuronal survival; and the hippocampus, involved in short-term memory.

The animals and tissues may be used in other applications of the invention to identify subsets of functionally activated cells. Non-limiting examples include neurons that are involved in brain function and activated in response to a stimulus or during an activity involving brain function; immune cells that are activated in response to a foreign agent or cell, including cells that are activated in a rejection response to a transplanted graft; cells that are activated in response to viral or bacterial infection; and cells that are activated in response to a wound or injury. Regulatory sequences for use in these embodiments of the invention may be readily identified as noted above by screening for gene expression activated by any of the above stimuli.

The invention may also be used for the identification of neural circuits and the cells that comprise them. The different subsets of neurons within the same brain or central nervous system area may be distinguished by use of the present invention into subsets that are stimulated and unstimulated. This provides evidence of circuitry that is involved in responses to particular stimuli, behaviors, tasks, and/or physiological states. As a non-limiting example, neurons that are in an excitatory or inhibitory circuit may be identified. Such neurons may form discrete neural ensembles that are employed for specific functions.

Additional non-limiting applications of the invention include identification of fetal cells in maternal blood. This may be practiced by introducing a nucleic acid construct of the invention into the cells of a pregnant or post-partum mother and activating cells via a cell surface receptor unique to the fetal cells (e.g. components of the major histocompatibility complex, or MHC, or the human lymphocyte antigen or HLA of the fetus). Methods for introducing nucleic acids into cells are known in the art, and one non-limiting example is via a pseudotyped viral vector with a broad target cell range. The fetal cells may then be detected as activated and identified as distinct from maternal cells, which would not be activated. The introduction of the nucleic acids and/or the detection of the activated cells may be performed ex vivo or in vitro as desired by the skilled practitioner. For example, maternal blood may be obtained and transformed with a nucleic acid construct of the invention in vitro followed by stimulation of a fetal specific receptor. The activated cells may then be readily identified.

The identified fetal cells may also be isolated and expanded. This may be advantageously applied to the isolation of fetal stem cells from an adult animal, including a postpartum human mother. A similar protocol can be used to identify adult stem cells in an animal, including a human being. Adult cells may be isolated in general and transfected with a nucleic acid construct of the invention comprising a regulatory sequence that is known to be expressed or inducible in stem cells. The regulatory sequence is then activated to permit identification of the adult stem cells.

The present invention also provides for characterization of neurons involved in behavioral sensitization. As a non-limiting example, activated neurons are identified after administration of a drug, such as cocaine, to an animal. Subsequent projection of neuronal structures such as axons or dendrites by these activated neurons may be labeled to identify the basis for increased sensitization to subsequent administration of the drug. This may also be applied to neuronal remodeling as part of learning or increases in experience. The invention may also be applied in relation to the cellular basis of long-term potentiation and long-term depression, such as during in vivo experience.

In another aspect, the present invention provides for the identification of an agent as functionally activating the same neurons as those activated in response to a stimulus or during an activity. A non-limiting example is identification of an appetite suppressing drug as activating the same neurons as activated upon satiety after eating. This application of the invention simply requires that the neurons activated by a particular agent be compared to the neurons activated in response to a stimulus or during an activity followed by determining whether the same neurons are activated.

After application of a stimulus or induction (or occurrence) of an activity, cells that are functionally activated may be identified by detecting the presence or intensity of the reporter. Where reporter expression is normally not detectable in cells, the simple presence of the reporter is sufficient to identify the cells as activated. Where there is some basal level of detectable reporter expression, an increase in the level of reporter expression or intensity is sufficient to identify the cells as activated. In a transgenic animal of the invention, the detection of reporter may be by examination of a region expected to contain activated cells for reporter luminescence or fluorescence. Microscopic examination in situ or in a tissue isolate permits the identification of individual cells as being activated. Appropriate invasive procedures, such as surgery, to provide access for identification of activated cells may be used as necessary for the practice of the invention.

Alternatively, the cells may be collected from the animal and analyzed in vitro. A non-limiting example is isolation of a tissue sample, such as a brain section or slice, expected to contain activated cells for identification of activated cells by detecting the reporter. Another example is isolation of cells apart from cells that are naturally found with them (e.g. liberation of cells from neighboring cells by digestion of intercellular attachments or fluorescent activated cell sorting, or FACS, of blood borne cells).

In another aspect of the invention, cells identified as functionally activated may be further studied or characterized. This may be conducted in situ within a transgenic animal, where cellular physiology of the identified cells is monitored with continuation of the activating stimulus or activity, after cessation of the activating stimulus or activity, or with introduction of a second stimulus (with or without cessation of the activating stimulus). As used herein, "cellular physiology" refers to biochemical activity of a cell, and non-limiting examples of further characterization include response to a chemical or drug agent, preparation of a gene expression profile, and subsequent cell growth.

Alternatively, further study or characterization may follow isolation of the identified cells as part of a tissue sample (e.g. a brain slice or section) from the animal or isolation of the cells from cells that are naturally found with them (e.g. FACS of blood borne cells that have been functionally activated). Non-limiting examples of further characterization include response to a chemical or drug agent, preparation of a gene expression profile, and subsequent cell growth. For example, immune cells identified as activated in response to transplantation of foreign tissue may be isolated by FACS and further characterized for their response to immune suppressive agents or candidate immune suppressive agents.

Where the identified cells are neurons, examples of further characterization include, but are not limited to, detection of electrophysiological changes, including changes in membrane potential (by whole cell recording techniques or use of dyes that are sensitive to ion movements), AMPA/NMDA ratios, glutamate receptor subunit composition, miniature EPSC analysis, threshold for action potential generation, short term plasticity including paired-pulse facilitation and paired-pulse depression, long term potentiation or depression, and sensitivity of plasticity events to pharmacological compounds. Identified neurons may also be studied for neuronal responses such as, but not limited to, increased firing rate, change in kinetics of opening and closing of one or more surface receptor channels, change in number of receptors, and depolarization. Additional studies may be made with respect to promotion of dendritic growth, actual changes in dendritic growth, and modification of synaptic function. As will be appreciated by those skilled in the art, the identified cells must remain viable for many of these subsequent analytical techniques.

As applied to transgenic plants, the present invention provides a readily available means to identify plant cells that are activated in response to particular stimuli or during particular activities. Non-limiting examples include response to light, injury, water or chemical agents such as herbicides and pesticides. Methods for the production of transgenic plants are known in the art and can readily be used to introduce the nucleic acids constructs of the invention.

Test or candidate drug as used herein refers to a chemically defined compound, such as organic molecules (large and small), inorganic molecules (large and small), proteins, peptides, nucleic acid molecules, oligonucleotides, lipids, polysaccharides, saccharides, or combinations or mixtures thereof the ability of which to functionally activate a cell is determinable by use of the present invention.

Unless defined otherwise all technical and scientific terms used herein have the same meaning as commonly understood to one of ordinary skill in the art to which this invention belongs.

Having now generally described the invention, the same will be more readily understood through reference to the following examples which are provided by way of illustration, and are not intended to be limiting of the present invention, unless specified.

EXAMPLE 1

Materials and Methods

Figure 2:
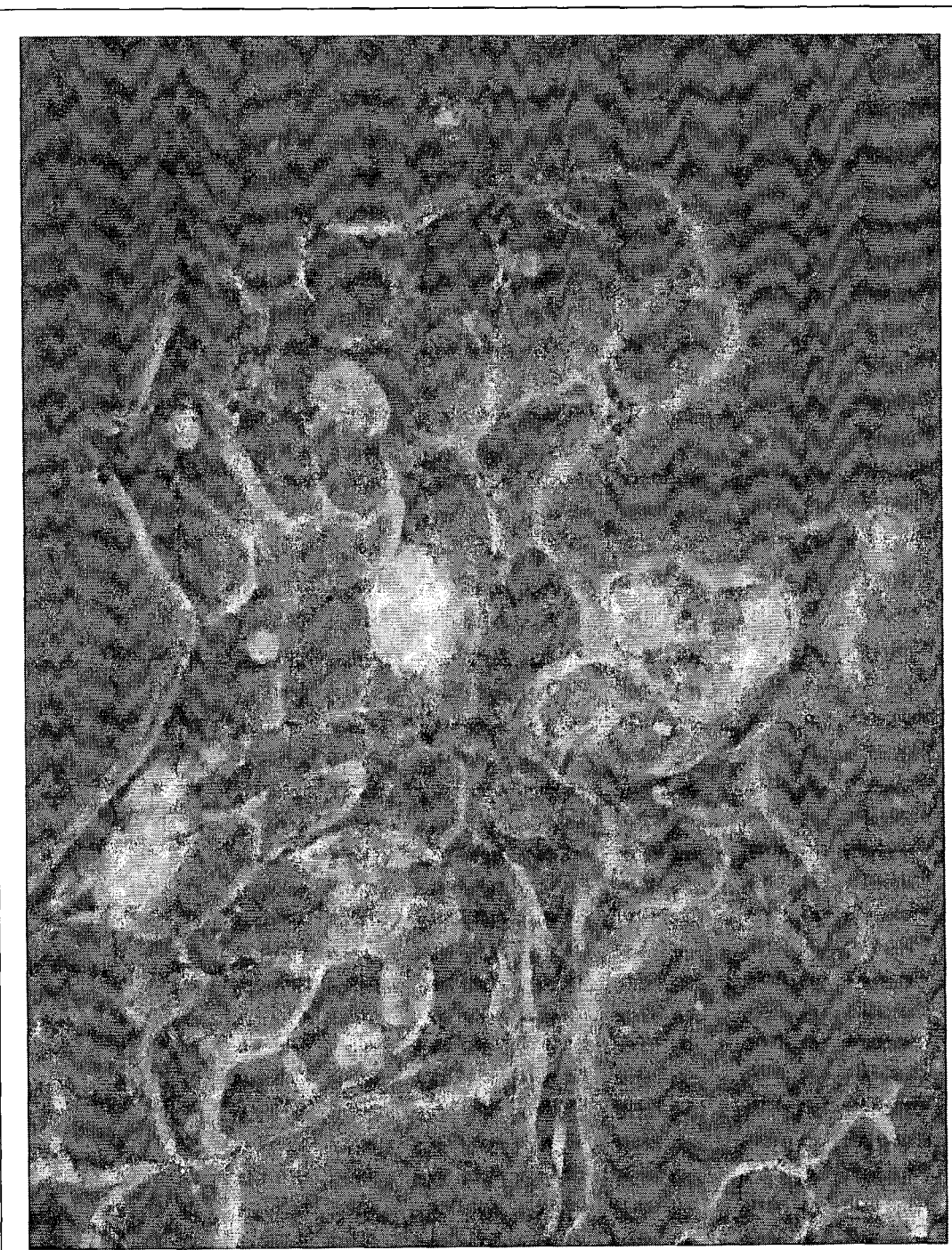
FIG. 2: GFP expression from a plasmid containing the construct of FIG. 1 was verified by $CaO_4$ transient transfection into 293 fibroblasts.

A c-fos and GFP fusion transgene (fosGFP) was constructed from a 6 kb HindIII-BamHI fragment that included the 5' untranslated region of the c-fos gene, encompassing the promoter as well as the complete genomic sequence of the c-fos gene, creating a fosGFP C-terminus fusion protein. The 5' end of the construct is derived from mouse genomic c-fos DNA (gift of T. Curran), beginning from a HindIII site 218 nucleotides from the first CRE binding site in the c-fos promoter (approximately 709 nucleotides from the start ATG codon), and includes all exon and intron sequences. The gene for EGFP has been fused (into the BamHI site) in frame to the last exon, and the polyA tail is derived from the pIRES-EGFP Clontech vector (FIG. 1). Thus, EGFP expression should follow c-fos activation. As used herein and the following Examples as well as the description of the figures, "GFP" expression or detection refers to expression or detection of EGFP. GFP expression was verified by $CaO_4$ transient transfection of the plasmid construct into 293 fibroblasts (see FIG. 2).

The linearized construct was excised from the vector and gel purified using the Qiaex II fragment purification system, where DNA was eluted into microinjection buffer containing 10 mM Tris-Cl, 0.1 mM EDTA, pH 7.4. The DNA solution was filtered using a 0.45 um spin filter (Millipore). The concentrated DNA solution (90 ng/µl) was injected into FVB single-cell mouse embryos, and nine founder lines were recovered. The founder lines are identified as 1-1, 1-2, 1-3, 4-1, 4-2, 4-3, 4-4, 5-1, and 6-1. Animals were backcrossed into C57B16J.

Germline transmission of the gene in each line was verified using PCR to detect the EGFP transgene. PCR primers were directed against regions of the EGFP transgene. Of the nine lines, one did not transmit the transgene to offspring. Transgenic lines were maintained as heterozygotes, and were crossed multiple generations (2-5) into C57B16. Animals were used at 4-12 weeks of age, and were maintained in single-sex cages with littermates (up to 5 per cage). For analysis of fosGFP expression under basal conditions, animals were not subject to any experimental protocol, and were sacrificed within 10 minutes of removal from their home cage with isoflurane anaesthesia followed by decapitation.

Transgene induction was verified using several different experimental protocols that are known to induce c-fos protein expression by in situ hybridization and immunohistochemistry. To induce fosGFP in the olfactory bulb, the animals were exposed to odorant for 10-90 minutes using either a 2-inch chunk of ripe banana in the cage, Juicy Fruit Chewing Gum™, or 1-10 µl of isoamyl alcohol spotted onto a filter paper either suspended above the holding area or directly on the cage bedding.

To induce fosGFP expression in somatosensory cortex, the animals were put into a novel environment with rich tactile stimuli for 1-18 hours to promote active whisking of the facial vibrissae. In some experiments, a portion of facial vibrissae had been removed since this results in a decrease of fos immunoreactivity in the sensory-deprived cortical areas.

In order to verify accurate expression of the transgene for sensory stimulation experiments, animals were subject to a single-whisker rearing protocol that is known to induce c-fos expression in the spared whisker barrel in the cortex (Staiger et al., 2002). Briefly, animals were anaesthetized with isofluorane and all but the D1 whisker from the large mystacial whisker pad were removed. Animals were then allowed to recover in their home cage for 24 hours. Animals were then sacrificed and tissue was prepared for slice electrophysiology or fixed directly in 4% paraformaldehyde in 0.1 M phosphate buffer.

A hypotonic saline injection was used to induce thirst (i.p., 2M NaCl, 100 µl/10 g body weight) 1-3 hours before animal sacrifice to activate fosGFP expression in the paraventricular nucleus (PVN) of the hypothalamus, an area of the hypothalamus implicated in osmoregulation. The animals were water deprived for 2 hours and then sacrificed or supplied with water ad libitum for a period of 2-6 hours to evaluate the persistence of fosGFP fluorescence after cessation of dehydration. Tissue was prepared for slice electrophysiology or fixed as indicated herein. The number of fosGFP+ cells within a fixed area of the PVN, from a single 50 µm thick tissue section for each animal, was assessed by two independent observers where both observers were blind to experimental condition. This approach may also be termed "osmotic stimulation."

For electrophysiology, animals were anaesthetized with isoflurane, and slices (100-400 µM) were prepared in ice-cold, bicarbonate-buffered solution (ACSF) saturated with 95% $O_2$/5% $CO_2$ (composition, in mM: 119 NaCl, 2.5 KCl, 1.0 $NaH_2PO_4$, 1.3 $MgCl_2$, 2.5 $CaCl_2$, 26.2 $NaHCO_3$ and 11 glucose). After preparation of slices, tissue was maintained at room temperature for the duration of the experiment in the same ACSF solution.

Expression of GFP and endogenous c-fos protein is performed by microscopy and anti-c-fos antibody labeling (Rinaman L. Interoceptive stress activates glucagon-like peptide-1 neurons that project to the hypothalamus. Am J Physiol 1999 August; 277(2 Pt 2):R582-90), respectfully, of tissue sections from transgenic mice following one of the above manipulations. Cells that co-express the two may also be confirmed, although it is possible that co-expression of GFP with c-fos protein is not always detectable due to the higher sensitivity of antibody based detection of c-fos versus fluorescent detection of GFP. This may provide an added advantage in that an increase in GFP expression upon stimulation of expression from the c-fos regulatory sequences is more readily detected. The sensitivity of c-fos detection may be attenuated by use of anti-c-fos antibodies with varying affinities (and thus sensitivities) for c-fos protein.

For immunohistochemistry, tissue was fixed for 2-12 hours at 4 C. and then sunk in a 30% sucrose/0.1 M phosphate buffer (PB) solution over a period of days. Floating sections (50 um) were prepared, and tissue was rinsed in 0.1 M PB prior to immunostaining. Sections were then washed in 0.1M PB with 0.1% Triton X-100 (PBT) for 30 minutes and blocked in PBT with 5% normal donkey serum (Jackson ImmunoResearch) for 1 hr. Primary antibody (Ab5 anti-Fos; Oncogene Science) was diluted 1:10,000 in blocking solution, and sections were incubated overnight at room temperature in this solution. Sections were washed in three changes of PBT, and then incubated in a Cy3-conjugated secondary antibody (Cy3 anti-rabbit; Jackson Immunoresearch) at a 1:500 dilution in blocking solution. Sections were then washed three times in PBT before being mounted in gelvatol and coverslipped on slides.

To compare expression of the fosGFP transgene with expression of the endogenous Fos protein, Fos-immunohistochemistry on tissue sections from the PVN of dehydrated wild-type littermates was performed. Antibody titer was adjusted to show comparable signal from immunoreactive and fosGFP fluorescent nuclei in order to provide a more accurate basis for comparison between these two signals, since high antibody titer is likely to provide an overestimate of Fos-immunoreactive (Fos-IR) nuclei due to signal amplification.

The number of Fos-IR nuclei immediately following 2 hours of dehydration was 59.5+4.5 (n=3) versus 3.25+1.75 for control, PBS-injected animals (n=2). In fosGFP transgenics (line 4-1), the number of fosGFP+ cells in the PVN after dehydration was 39.3+4 (n=3) versus 2.5+1.2 for control, PBS-injected animals (n=3). Thus, although the number of Fos-IR cells in wild-type animals was higher than the number of fosGFP+ cells in fosGFP transgenics, the numbers were roughly comparable. In this way, the fosGFP mice may be useful as a surrogate for Fos immunohistochemistry, providing a high-throughput platform for in vivo pharmacology For imaging and quantitation of double-labeled cells, photographs of living or immunostained tissue were taken with a Retiga 1300 CCD cooled camera (Q Imaging; Southern Micro Instruments, Inc.) mounted on an Olympus BX51 W1. Low magnification pictures were taken using an Olympus XLFluor4X/340 objective with a 0.28 NA. However, green fluorescent cells were frequently bright enough to be visible at low magnification (4X) through the eyepiece of the microscope, without signal integration through the camera.

To observe persistence of fosGFP fluorescence ex vivo and for electrophysiology, slices were maintained in bicarbonate-buffered solution (ACSF) saturated with 95% $O_2$/5% $CO_2$ at room temperature. To avoid GFP bleaching or fluorescence-induced toxicity in experiments where the same area of brain was imaged repeatedly over a period of hours, the tissue was illuminated for a short period of time, typically about 10 seconds, to focus and record the image.

EXAMPLE 2

Figure 3:
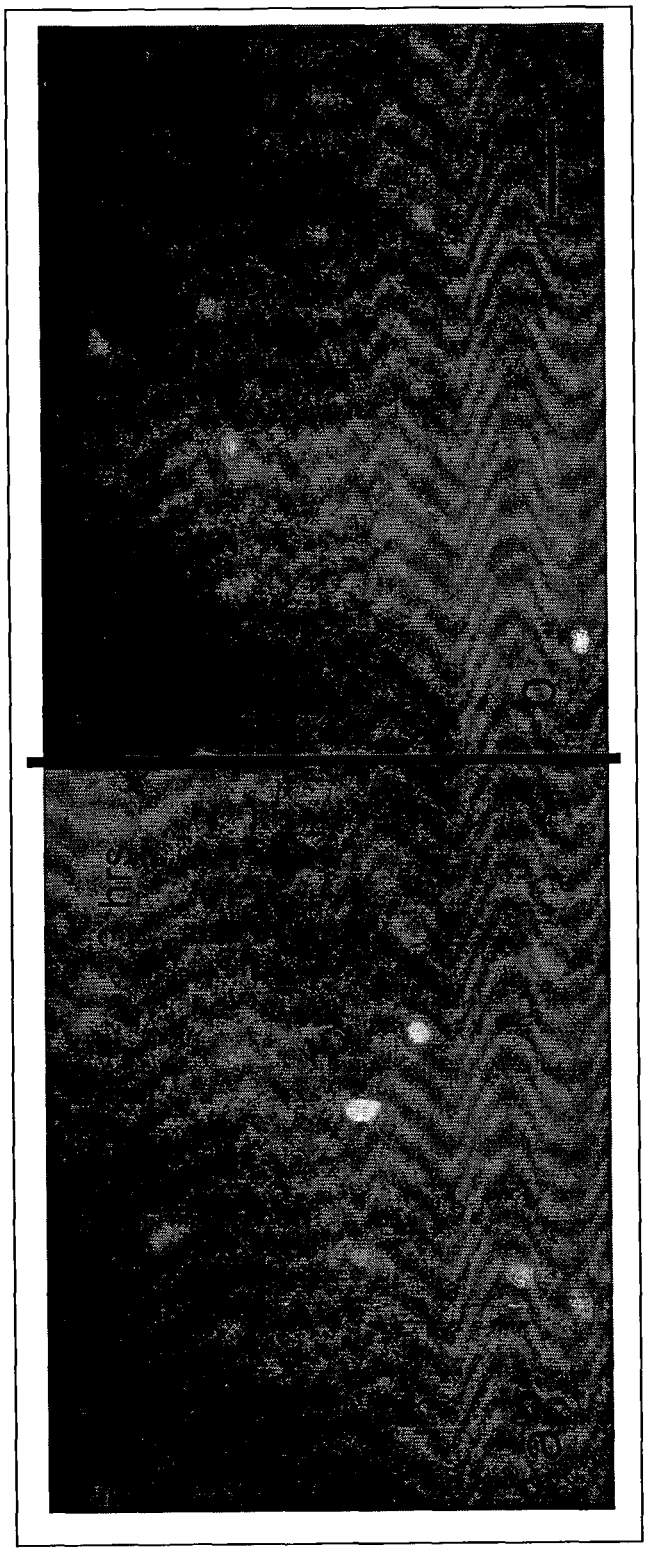
FIG. 3 shows the persistence of c-fosGFP expression persists in neocortex tissue of living brain slices.

Fluorescence in Living Neocortex Tissue c-fosGFP expression persists in neocortex tissue of living brain slices for long periods of time. Transgenic mice from line 1-3 were housed in a novel environment for 1-3 hours before sacrifice to encourage exploratory behavior using facial vibrissae. GFP-expressing cells within barrel (somatosensory) cortex were observed in all layers although they were more frequent in layer IV. The brain was dissected out into cold PBS and were maintained in room-temperature oxygenated Ringer's solution for the period of time indicated. Brain slices (400 μm) were prepared and imaged directly afterward in an intact unfixed preparation. See FIG. 3, where Panel a shows barrel cortex layer IV, 3 hrs after slices were prepared. Panel b shows the barrel cortex, 5 hrs after slices were prepared. GFP-expressing cells were visible in the tissue throughout the timecourse. Bar=approximately 50 μm.

EXAMPLE 3

Induction of Response to Thirst

Figure 4:
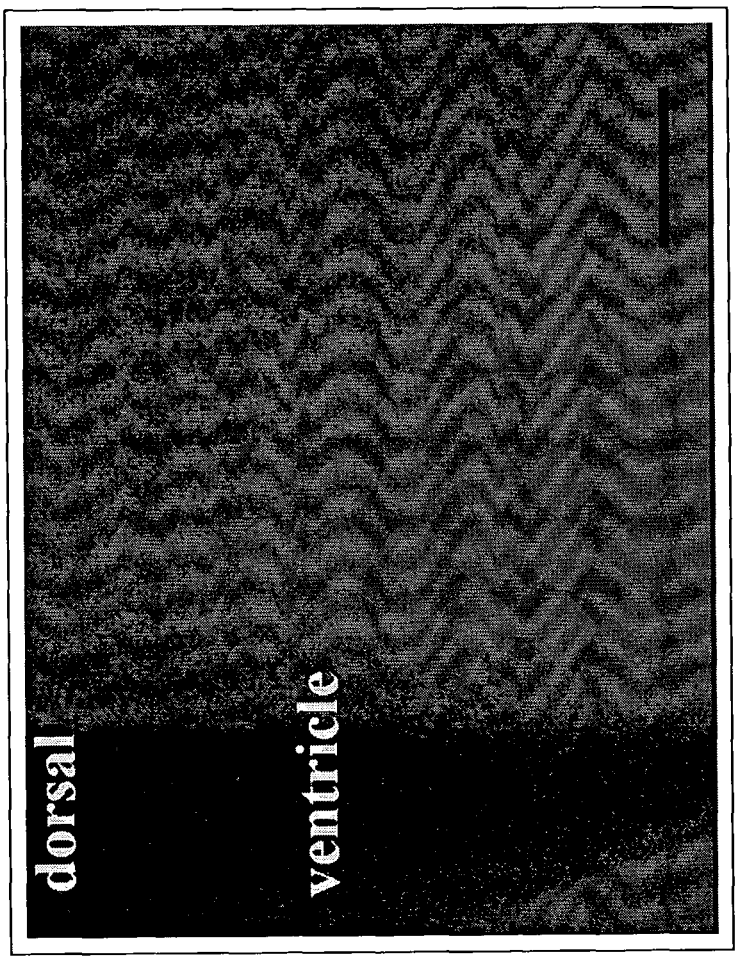
FIG. 4 shows activation of a GFP-expressing cell in the paraventricular nucleus of the hypothalamus after hypotonic saline injection.

Subcortial activation of c-fosGFP by hypotonic saline injection was performed. Mice from line 4-4 were injection with hypotonic saline (100 μl per 10 g body weight, 2M NaCl, i.p.) to induce osmotic imbalance (thirst) 1.5 hrs before animal sacrifice. Living brain slices (400 μm) were cut using a vibratome in oxygenated Ringer's solution and were maintained in room-temperature oxygenated Ringer's solution. The sections were viewed under fluorescence microscopy. Multiple GFP-expressing cells were detected in the paraventricular nucleus of the hypothalamus at least 4 hrs. after saline injection. FIG. 4 shows a view containing a single GFP expressing cell (bar=approximately 50 μm).

EXAMPLE 4

Levels of Transgene Expression

Figure 5:
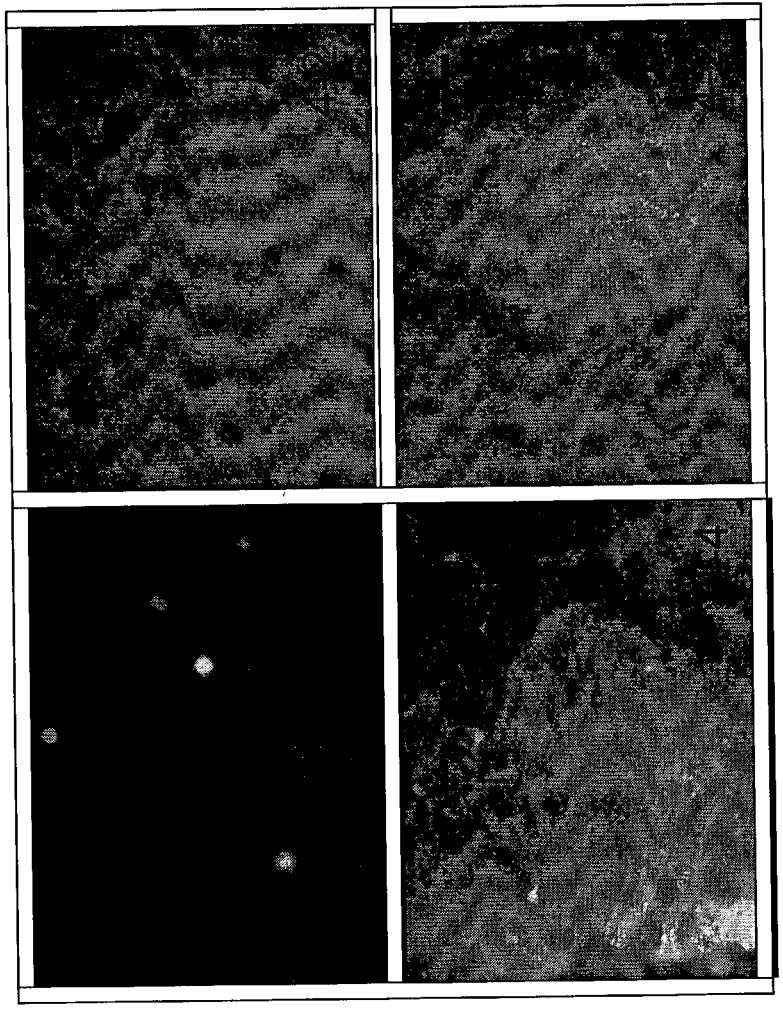
FIG. 5 shows different levels of transgene expression between founder lines.

Different founder lines showed varying levels of transgene activation under similar circumstances. Animals from three different transgenic lines (1-3, 4-2, and 4-4) were stimulated using whisker stimuli (novel environment) or odorant (isoamyl alcohol) to induce c-fosGFP expression as indicated in the previous Examples (see FIG. 5). Line 4-4 showed very low levels of GFP-expressing cells, and may have a higher threshold for transgene activation. Bar=approximately 2 μm.

EXAMPLE 5

Figure 6:
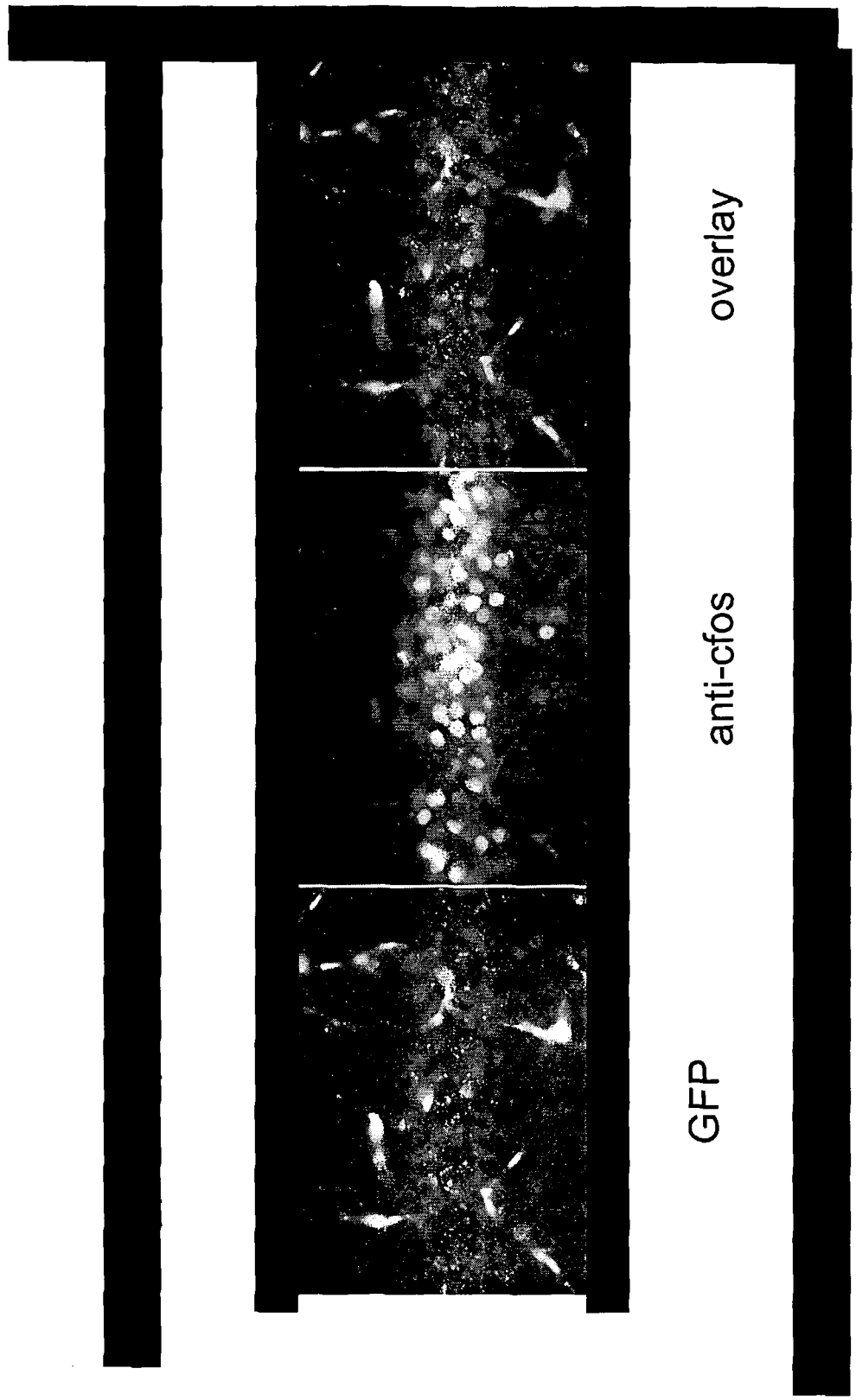
FIG. 6 shows the overlap of c-Fos immunohistochemistry and GFP expression in cells of the hippocampus.

Hippocampus Expression of c-fos and GFP c-Fos immunohistochemistry and GFP expression were observed to overlap in the hippocampus. Tissue from a transgenic mouse (line 1-2) stimulated by a novel environment 2 hrs prior to sacrifice was cut into living brain slices (400 μm thick) in an oxygenated Ringer's solution using a vibratome. Slices were later fixed in 4% paraformaldehyde and resectioned into 50 μm thick sections and then processed for c-fos immunohistochemistry using an antibody generated against amino acids 4-17 of synthetic c-Fos protein (gift of L. Rinaman, University of Pittsburgh and P. Larsen and J. Mikkelsen, Panum Institute, Denmark) at a dilution of 1:50,000. Panel a of FIG. 6 shows GFP labeled cells, which are green in Panel c. Panel b shows c-Fos immunoreactive cells visualized with a Cy3 secondary antibody, which are red in Panel c. Panel c shows an overlay of Panels a and b where yellow indicates overlapping expression. Because immunological detection of the fos antigen is amplified with a secondary antibody, the red signal is much stronger than the GFP signal.

EXAMPLE 6

Figure 7:
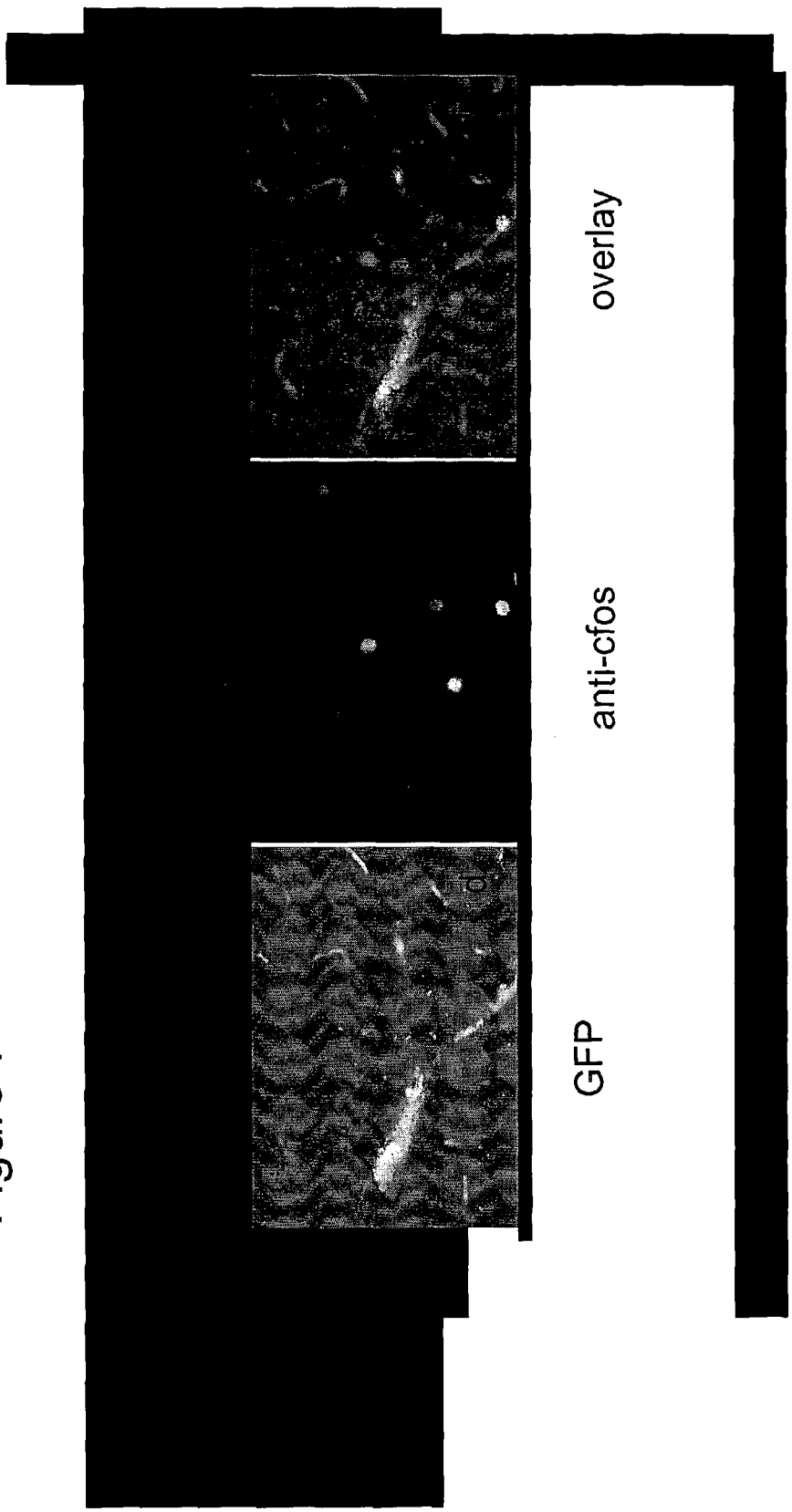
FIG. 7 shows the overlap of c-Fos immunohistochemistry and GFP expression in cells of the neocortex.

Neocortex Expression of c-fos and GFP c-Fos immunohistochemistry and GFP expression were observed to overlap in the neocortex. Tissue from barrel cortex of a transgenic mouse (line 1-2) stimulated by a novel environment 2 hrs prior to sacrifice was processed for c-fos immunohistochemistry as described in Example 4. Panel d of FIG. 7 shows GFP labeled cells, which are green in Panel f. Panel e shows c-Fos immunoreactive cells visualized with a Cy3 secondary antibody, which are red in Panel f. Panel f shows an overlay, where yellow indicates overlapping expression. Because immunological detection of the fos antigen is amplified with a secondary antibody, the red signal is much stronger than the GFP signal.

EXAMPLE 7

Induction of Single Barrel in Response to Uniwhisker Rearing

Figure 8:
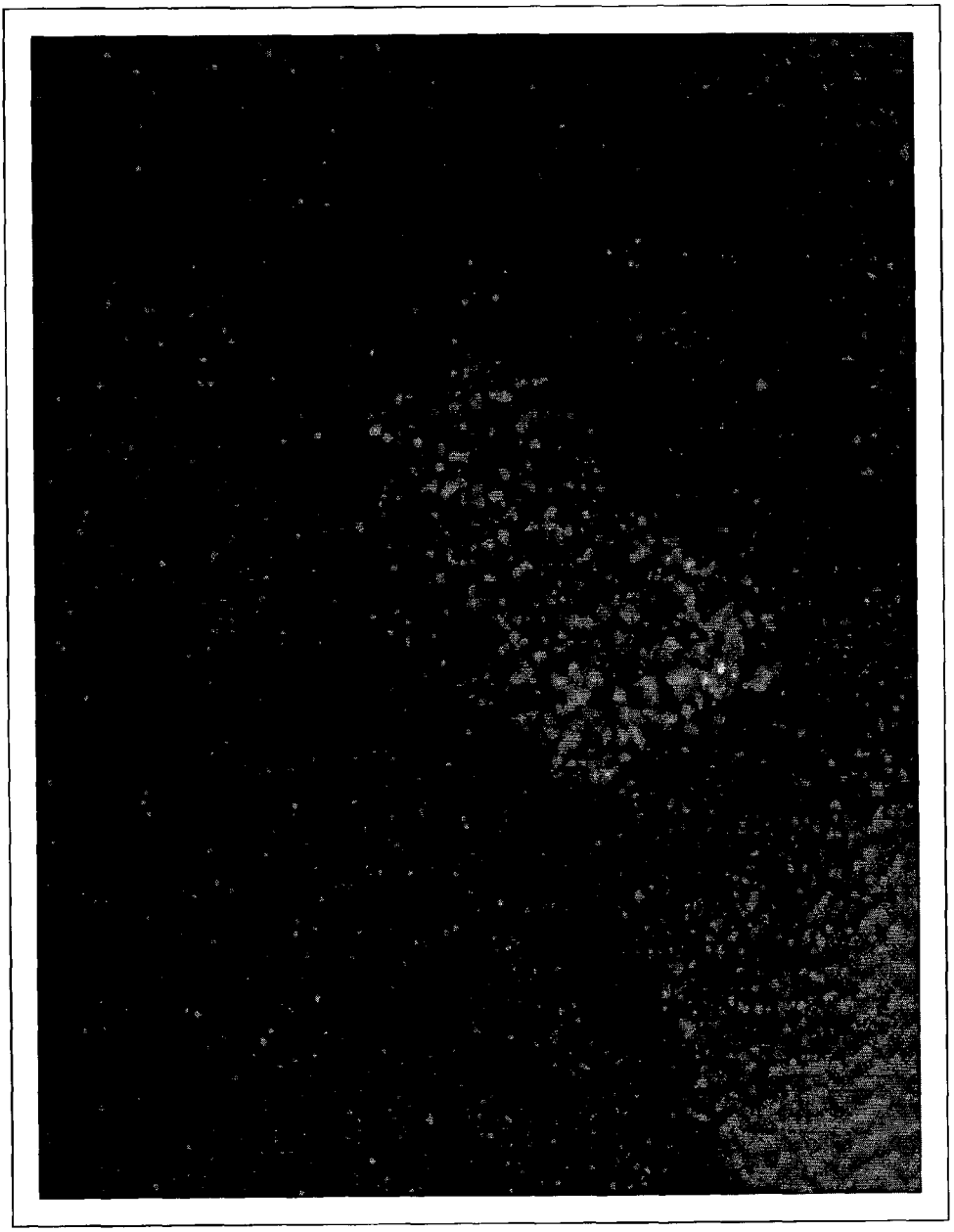
FIG. 8 shows induction of GFP expression in a single barrel within the barrel cortex in response to uniwhisker rearing.

Uni-whisker rearing was observed as inducing c-fosGFP expression in a single barrel within the barrel cortex. A transgenic mouse (line 1-2) was subjected to univibrissae-rearing, where all but one whisker was removed from one side of the snout for a period of 18 hours. The brain was removed and fixed for several hours, and then the cortex was flattened and cryoprotected in sucrose. This preparation allows visualization of all the barrels in layer IV upon sectioning. Fifty μm-thick sections were prepared and scanned for GFP-expressing cells. A single barrel corresponding to the C1 whisker was heavily labeled with GFP-expressing cells (see FIG. 8), whereas the surrounding, sensory deprived barrels show little or no GFP-expressing cells. Bar=100 μm.

EXAMPLE 8

Characterization of fosGFP Transgenic Mice

Of nine founder lines, one line did not produce transgenic offspring, and two other lines did not show appreciable levels of fosGFP expression in the brain. Six lines showed approximately >30% transmission of the transgene after multiple backcrosses to C57B16, and were further evaluated (see Table 1). The transgene was maintained in heterozygotes, and transgenic animals were viable and showed a normal lifespan (1+ year). Of the six lines subjected to further characterization, expression in multiple brain areas including hippocampus, cerebellum, olfactory bulb, and neocortex under basal conditions was examined (data not shown). Transgenic lines differed with respect to basal levels of gene expression in different brain areas. Under basal conditions, little or no fosGFP expression was observed in the cerebellum. Expression in the olfactory bulb was also variable between lines. Hippocampal and neocortical expression was observed in all transgenic lines.

TABLE 1

Summary of initial evaluation of fosGFP transgenic lines.

| line | percent transgenic[#] | percent of transgenics with GFP fluorescence |
|---|---|---|
| 1-1 | 59.5 (*n = 74*) | 50.0 (*n = 6*) |
| 1-2 | 49.2 (*n = 185*) | 46.2 (*n = 13*) |
| 1-3 | 58.1 (*n = 129*) | 82.6 (*n = 23*) |
| 4-1 | 48.8 (*n = 246*) | 100 (*n = 34*) |

TABLE 1-continued

Summary of initial evaluation of fosGFP transgenic lines.

| line | percent transgenic# | percent of transgenics with GFP fluorescence |
|---|---|---|
| 4-2 | 48.5 (n = 103) | 46.2 (n = 13) |
| 4-4 | n/a* | n/a* |
| 4-5 | 33.0 (n = 91) | 55.6 (n = 9) |
| 5-1 | 54.3 (n = 208) | 76.5 (n = 17) |
| 6-1 | 26.4 (n = 174) | 90.9 (n = 11) |

Animals were bred as heterozygotes and were crossed to wild-type C57/bl6 mice 1-5 generations. Percentages reflect the number of transgenics/wild-type + transgenics for all backcrosses in a given line. The number of transgenic animals in a litter was expected to be 50%, if transgene inheritance was Mendelian. The total number of animals, both transgenic and wildtype, that were genotyped is listed in italics.
^Not all transgenic animals exhibited fosGFP fluorescent cells in the brain under stimulated or basal conditions. The penetrance of transgene expression was assessed by the presence of fosGFP fluorescence in the CNS by inspection. The total number of transgenic animals examined for this criterion is listed in italics.
*Line 4-4 showed no transgenic offspring in the first backcross, and was not subject to further analysis.

EXAMPLE 9 fosGFP Induction in Barrel Cortex

Figure 9:
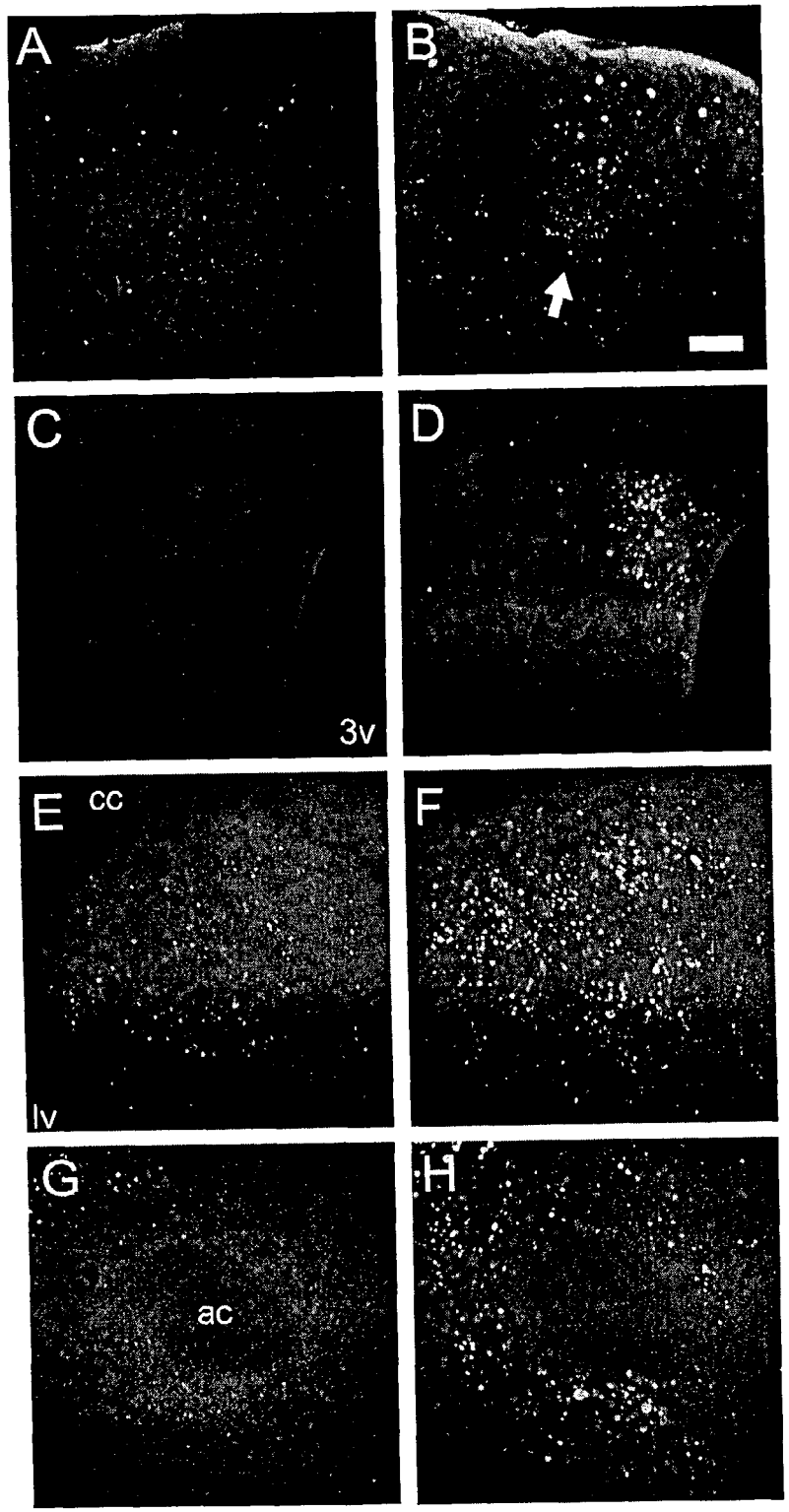
FIG. 9 shows fosGFP induction after sensory, physiological, and pharmacological stimulus.

Single-whisker rearing has been shown to induce gene expression in the barrel cortex within a few hours (Barth et al., 2000; Rocamora et al., 1996; Staiger et al., 2000; Staiger et al., 2002). This gene expression may proceed by a CREB-dependent pathway and may be related to the induction of plasticity in the neocortex (Barch 2000). Preliminary evidence suggested that CRE-mediated gene transcription and c-fos expression occurred in the same subset of cells, which is not surprising given that the c-fos promoter contains a CRE site. fosGFP transgene induction after plucking all but one of the large mystacial vibrissae, whisker D1, was investigated. To verify that expression was restricted to the spared whisker barrel, some brains were flattened after fixation so that individual barrels could be identified in a tangential plane of section. In these cases, cells in layer IV were clearly labeled with GFP in the spared barrel, whereas cells in adjacent, deprived barrels showed little expression. The spared barrel was also identifiable in coronal sections of fixed tissue, and because this preparation enabled us to observe layer-specific patterns of gene activation, was used for subsequent analysis (FIG. 9, panel A). The greatest number of labeled cells was in layer IV. A subpopulation of cells in supragranular layers expressed high levels of GFP, brighter than that observed in layer IV, and GFP-expressing neurons were also observed in infragranular layers. For both supra- and infragranular layers, GFP-expressing cells were not precisely restricted to the barrel column, as has also been observed with Fos immunohistochemistry. On the contralateral side corresponding to the spared sensory input, fosGFP+ cells were scattered throughout the tissue and were not concentrated in the area of a single barrel (FIG. 9, panel B).

EXAMPLE 10 fosGFP Induction in PVN After Dehydration

A dehydration stimulus was used to evaluate fosGFP expression in subcortical areas, as distinct from the neocortex. Transgenic animals were injected with a concentrated saline solution (to induce serum hypertonicity) and also deprived of water, a protocol that activates the magno- and parvocellular neurons of the paraventricular nucleus (PVN). This treatment has been shown to induce robust c-fos expression in this brain area. Hypertonic saline injection into fos-GFP animals induced strong GFP fluorescence in neurons of the PVN (FIG. 9, panels C and D), comparable to what had been observed using in situ hybridization or immunohistochemical techniques (Giovannelli et al., 1990). Control animals injected with isotonic phosphate-buffered saline showed few if any GFP-expressing neurons within these brain areas. Significant dehydration-induced activation of fosGFP expression in the PVN was observed in two transgenic lines, 4-1 and 6-1.

EXAMPLE 11

Pharmacological Induction of fosGFP

The atypical antipsychotic clozapine has been a successful agent for the treatment of schizophrenia and dementia. Because of its therapeutic relevance, clozapine was selected as a pharmacological agent to monitor transgene induction in the fosGFP transgenic mice. Although its mechanism of action in different brain areas is unclear (it has affinity for dopamine, serotonin, adrenergic, and cholinergic receptors) administration of this drug induces a characteristic pattern of c-fos expression throughout the CNS (Wan et al., 1995). Indeed, a better understanding of how this compound alters neural activity and induces c-fos expression in distinct populations of neurons is expected to improve efforts at developing new therapeutically relevant compounds.

Clozapine administration induced fosGFP fluorescent neurons in a variety of brain areas that have been shown to express c-fos under these conditions, whereas PBS-injected animals showed little or no signal in the comparable brain areas. In particular, fosGFP+ neurons in prefrontal/cingulated cortex, the lateral septal nucleus, regions of the nucleus accumbens, and the striatum were monitored. Two fosGFP transgenic lines, 1-3 and 5-1, showed strong fosGFP induction compared to control PBS injected animals (FIG. 9, panels E-H; line 5-1).

EXAMPLE 12 fosGFP Detection in Living Brain Tissue

Figure 10:
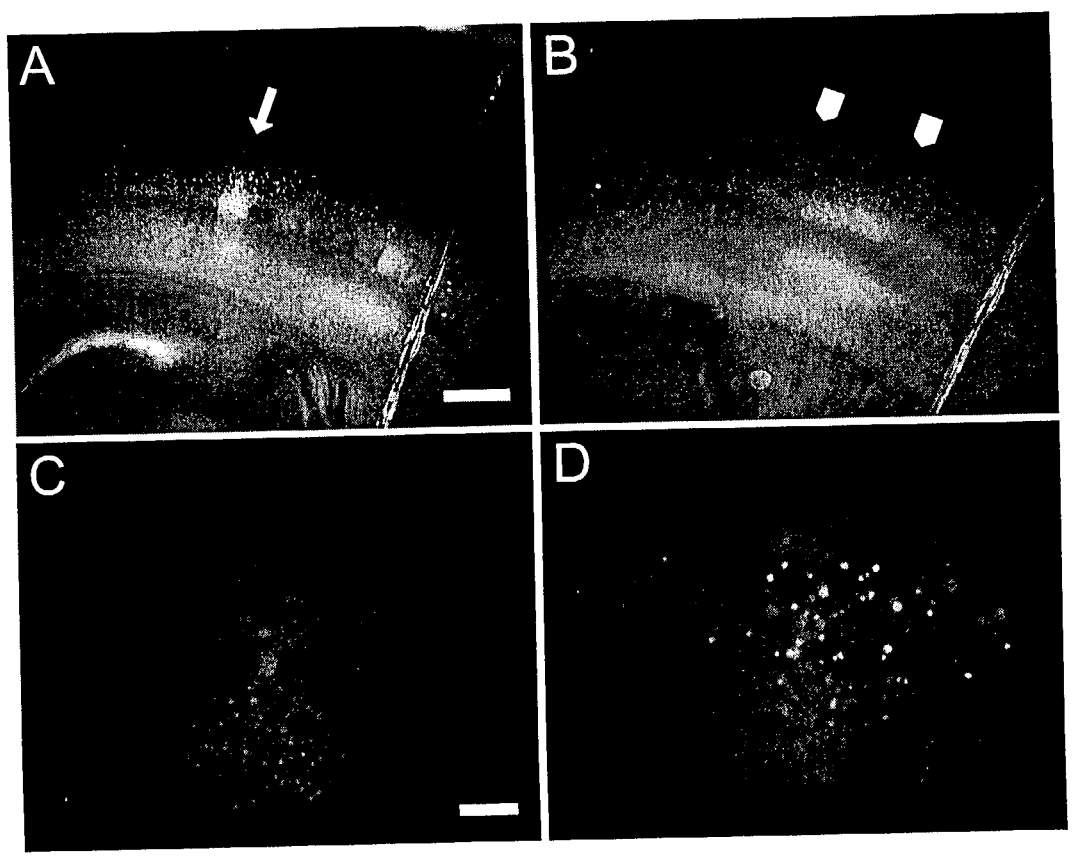
FIG. 10 shows fosGFP expression is visible in living brain slices.

The GFP-expressing cells were also visible in coronal cross-section in living brain slices, under several experimental conditions (FIG. 10). All but a single large facial vibrissa, whisker D1, were removed by plucking from a fosGFP transgenic (line 4-1) aged approximately 4 weeks. The animal was returned to its home cage for 24 hours before brain slices were prepared.

After single-whisker rearing, GFP-fluorescent cells were visible in a single barrel in S1, while adjacent deprived barrels showed few or no fosGFP-expressing cells. fosGFP fluorescent cells in the spared barrel were visible in all cortical layers, with the largest number of cells labeled in layer IV. Labeled and non-labeled cells were intermingled within a barrel, suggesting that different subpopulations of cells might be differentially activated by single-whisker rearing, as has been observed with Fos immunohistochemistry (Staiger et al., 2002). Boundaries of the spared and deprived sensory regions were clearly visible in layer IV. Because the tissue was thicker than the fixed sections and there were many layers of GFP-expressing cells within a given field of view, it was more difficult to resolve individual cells in living brain slices. However, some bright GFP cells were close enough to the surface to enable clear visualization and whole-cell recording.

In some cases, animals were subjected to single-whisker rearing and whole brains were dissected and maintained in oxygenated ACSF during a brief period of inspection using a conventional fluorescence microscope with a 4×, 0.28 N/A objective. Even under these somewhat rudimentary conditions, a small cluster of fosGFP-expressing cells in the area of S1 could be detected (data not shown), indicating that the fosGFP+ cells may be targeted for in vivo electrophysiological recording.

EXAMPLE 13

In Vivo Timecourse of fosGFP Fluorescence

To determine the half-life of the fosGFP fusion protein in vivo, the persistence of fosGFP fluorescence induced by dehydration in the PVN was examined for a period of hours following reintroduction of water. Fos protein shows maximal induction 1-2 hours after saline injection and disappears by approximately 4 hours after water has been reintroduced to the experimental animals. In other examples of Fos protein persistence, the half-life of the protein after induction has been found to be at least 2 hrs, although it can be as short as 30 minutes in some cell lines (Curran and Morgan, 1986; Muller et al., 1984).

Figure 11:
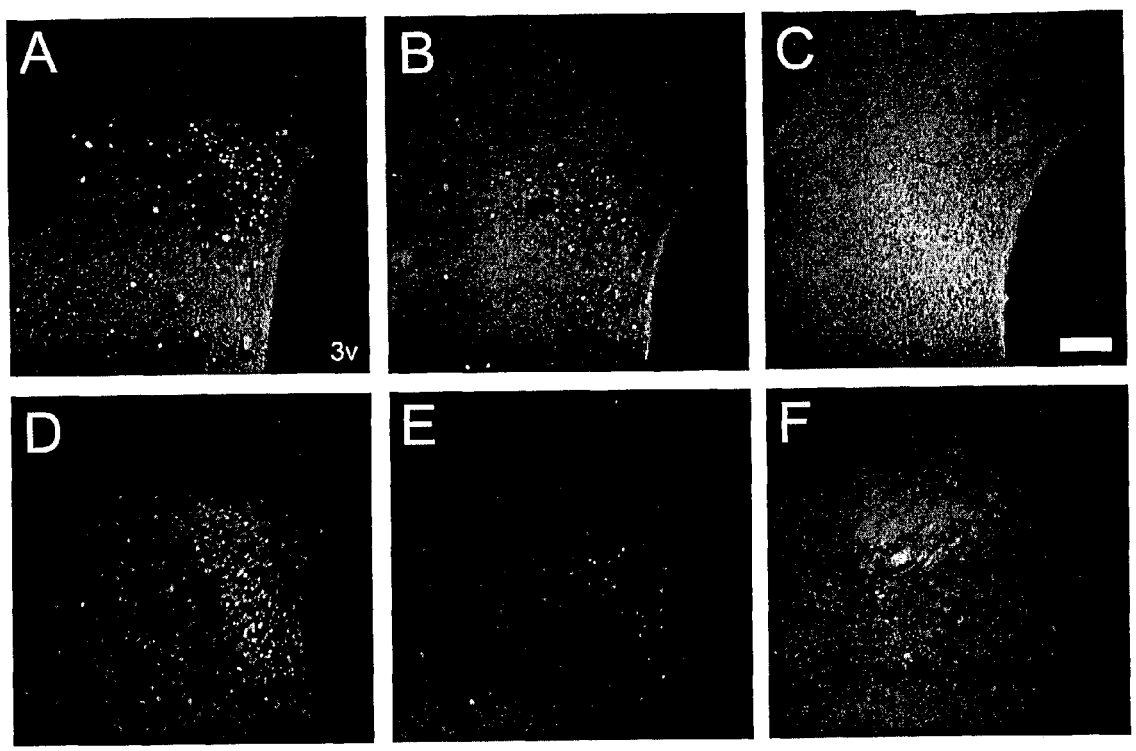
FIG. 11 shows duration of fosGFP fluorescence after in vivo stimulation. Panels A-C show fosGFP transgenic animals (4-1) and their wild-type littermates (panels D-F) were injected with hypertonic saline as a dehydration stimulus, and simultaneously deprived of water for 2 hours, and fosGFP expression (panel A) or Fos-IR (panel D) was examined in the PVN at this time. Water was reintroduced ad lib, and fosGFP or Fos-IR was determined at 2 (panels B and E) and 6 (panels C and F) hours following water reintroduction. The number of fosGFP+ cells and the number of Fos-IR at each timepoint was calculated to determine the half-life of fosGFP versus endogenous Fos. Bar=100 μm.

The number of fosGFP fluorescent cells within the PVN was calculated from animals sacrificed at 0, 2, 4 and 6 hours after reintroduction of water ad libitum (FIG. 11). As a basis for comparison, the number of Fos-IR cells from wild-type littermates was also calculated at the same timepoints. The half-life of fosGFP signal in the PVN was similar for that of Fos-IR (approximately 5 hours), as assessed by calculation of fluorescent nuclei at 0, 2, 4, and 6 hrs following resolution of the dehydration stimulus (n=2-3 wild-type animals per timepoint; n=3-4 transgenic animals per timepoint), and was similar to that which has been observed for Fos-IR in the PVN previously (Sharp et al., 1991).

EXAMPLE 13 fosGFP Fluorescence Ex Vivo

Figure 12:
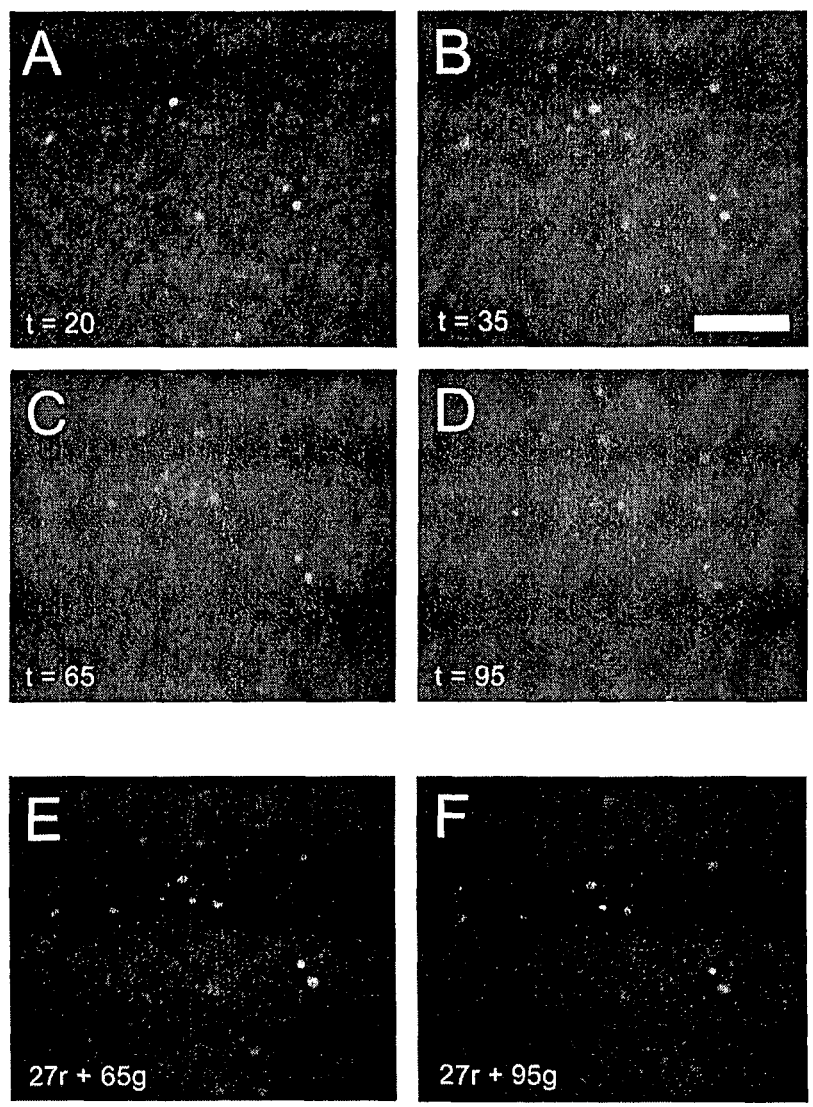
FIG. 12 shows preparation of brain slices does not induce fosGFP expression. Brain slices from a control fosGFP transgenic animal were made and examined shortly after tissue preparation. In all panels, t=0 is time of decapitation. Panels A-D show a region of cortex was imaged at multiple timepoints. Arrow indicates a cell whose fluorescence decreases over the time period examined. Panels E and F show images from early timepoints were color-coded red and overlaid upon images from later timepoints color-coded green. In this case, cells whose fluorescence disappears would appear red, and cells where new fosGFP expression was induced would appear green. No new fosGFP expressing (green) cells arose in the field examined. Panel E shows an image from t=27 minutes (red) was merged with an image from t=65 minutes (green). Red cells are those cells whose GFP fluorescence decreased over this time period, and yellow cells are those cells that can be identified in both images. The snapshot from t=27 was used for the merged picture because of slight differences in the distance between labeled cells due to spreading of the tissue after being positioned in the observation chamber. Panel F shows an image from t=27 minutes (red) was merged with an image from t=95 minutes (green). Note the large number of red cells and the absence of any (new) green cells in this comparison. Bar=50 μm.

Patterns of gene expression in living tissue were identical to that observed in fixed tissue. However, ischemic and mechanical trauma during brain dissection and slice preparation might activate fosGFP expression over time. This might impede efforts to electrophysiologically identify neurons specifically activated by in vivo stimuli. In order to examine this possibility, brain slices from fosGFP mice were prepared and examined for several hours after slice preparation (FIG. 12). Areas of analysis included the barrel cortex, the hippocampus, and olfactory cortex. In general, the field of view included approximately 50-250 cells. During a period of 2-3 hours in the slice recording chamber, the number and intensity of GFP-fluorescent cells decreased. In no case was unambiguous detection of new GFP-fluorescent cells observed during this time period. GFP-expressing cells, however, could be quite long-lived within a brain slice and on some occasions could be observed up to nine hours post-slicing.

As an additional control, sections of living brains from fosGFP transgenics and their wild-type littermates were obtained and fixed slices 0-3 hours after cutting. Fos-IR was determined (in the case of wild-type samples) or fosGFP fluorescence was examined at each timepoint. No detectable fosGFP expression was observed and only scattered Fos-IR neurons at all timepoints within this period. Tissue preparation apparently does not induce significant fosGFP fluorescence in the transgenic lines examined.

Of particular interest was the longevity of GFP fluorescence in a brain area where c-fos expression had been induced in vivo. To address this issue, brain slices from single-whisker reared animals were prepared, and the spared whisker barrel was identified and imaged repeatedly over a period of several hours. Initially, the highest concentration of GFP fluorescent cells was in layer IV of the spared barrel, with a scattering of bright cells in supra- and infragranular layers. The number of identifiable GFP fluorescent cells decreased over time, such that after several hours the number of fosGFP fluorescent cells had nearly disappeared in layer IV, although many cells were still visible in deep and superficial layers of the spared barrel.

Figure 13:
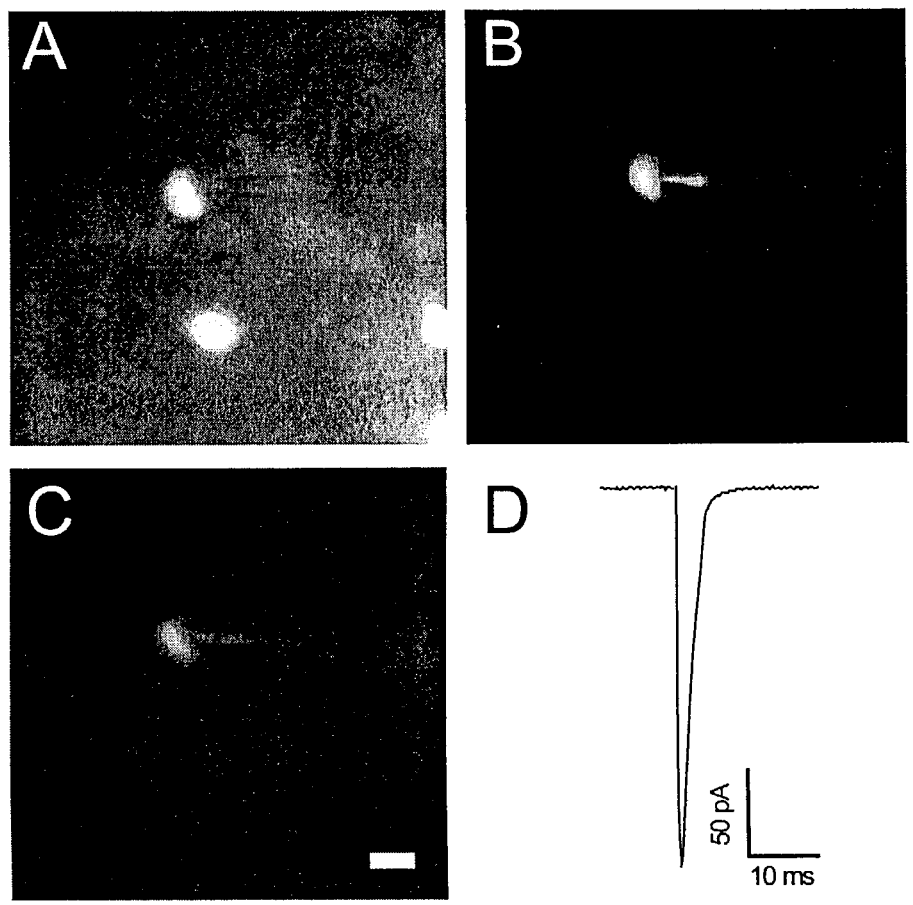
FIG. 13 shows whole-cell recording from fosGFP-expressing neurons. fosGFP+ cells from layer II/III of barrel cortex from a P12 transgenic mouse were targeted for whole-cell voltage-clamp recording. Panel A shows fosGFP+ nuclei. Panel B shows patch solution contained the red fluorescent dye Alexa-568 (10 μm) to fill the targeted cell. Panel C shows merged picture of A and B shows that the Alexa-filled cell has a fosGFP+ nucleus. Bar=30 μm. Panel D shows EPSCs were evoked by stimulation of superficial layers of an adjacent barrel. Sample EPSC (holding −72 mV) from the cell in panels A-C.

GFP-fluorescent cells were easily visible for sufficient time to allow for targeted whole-cell recording. fosGFP+ neurons were patched in voltage-clamp configuration, and filled with the red fluorescent dye Alexa568 to verify that the patched cell was indeed fosGFP fluorescent (FIG. 13). GFP-fluorescent cells were viable and displayed typical glutamatergic synapses under these conditions (FIG. 13, panel D). Based upon this data, the feasibility of recording from fosGFP+ cells activated by a wide variety of in vivo stimuli in order to examine their electrophysiological properties as well as the characteristics of particular synaptic inputs onto these cells is demonstrated.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation. The invention also includes all of the steps, features, compositions and compounds referred to or indicated in this specification (unless specifically excluded) individually, collectively, and any and all combinations of any two or more of said steps or features.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of identifying one or more living sensory neurons activated by a stimulus in a transgenic mouse, said method comprising:
    (a) providing a transgenic mouse whose genome comprises a nucleic acid construct comprising the c-fos 5' untranslated region, which comprises one or more regulatory sequences and the complete genomic sequence of the c-fos gene fused in frame to a detectable reporter, wherein the one or more regulatory sequences is activated in a sensory neuron in response to a predetermined chemical, behavioral, or pharmacological stimulus,
    (b) administering the predetermined chemical, behavioral, or pharmacological stimulus to the transgenic mouse of step (a),
    (c) identifying ex vivo in a brain slice derived from the transgenic mouse in step (b) one or more living sensory neurons expressing the detectable reporter, while maintaining the sensory neuron's viability, and wherein the detectable reporter is a luminescent or fluorescent protein.

2. The method of claim 1, wherein the fluorescent protein is selected from the group consisting of green fluorescent protein (GFP), enhanced green fluorescent protein (EGFP), yellow fluorescent protein, cyan fluorescent protein, blue fluorescent protein, red fluorescent protein, HcRed, and analogs thereof, or the luminescent protein is luciferase or an analog thereof.

3. The method of claim 1, wherein the transgenic mouse has progeny and the progeny of the mouse each have a genome comprising said nucleic acid construct.

4. The method of claim 1, wherein the predetermined chemical, behavioral, or pharmacological stimulus is administration of a drug, pain, or pleasure; induction of dendritic outgrowth; or learning.

5. The method of claim 4, wherein the learning is selected from the group consisting of an elevated plus maze, a light/dark box, an open field test, and a water maze.

6. The method of claim 1, wherein the predetermined chemical, behavioral, or pharmacological stimulus is selected from the group consisting of fear; sensory deprivation or stimulation; stress; reward for behavior that the mouse attends to; conditioning; visual, audio, location or olfactory cues; administration of a mind altering drug selected from the group consisting of nicotine, marijuana, cocaine, heroin, alcohol, and functional equivalents thereof; mating; aggression; sexual behavior, maternal behavior; social dominance; and deprivation of water or food.

7. The method of claim 6, wherein the location cue is linked to drug addiction.

8. The method of claim 7, wherein the drug is selected from the group consisting of nicotine, marijuana, caffeine, cocaine, heroin, and alcohol.

9. A method of identifying one or more living sensory neurons activated by stimulus in a population of isolated sensory neurons, said method comprising:
(a) providing a transgenic mouse whose genome comprises a nucleic acid construct comprising the c-fos 5' untranslated region, which comprises one or more regulatory sequences and the complete genomic sequence of the c-fos gene fused in frame to a detectable reporter wherein the one or more regulatory sequences is activated in a sensory neuron in response to a predetermined chemical, behavioral, or pharmacological stimulus,
(b) administering the predetermined chemical, behavioral or pharmacological stimulus to the transgenic mouse of step (a),
(c) isolating a population of sensory neurons from the brain of the transgenic mouse in step (b), while maintaining the sensory neuron's viability, and
(d) identifying a living sensory neuron expressing the detectable reporter in a population of living sensory neurons, wherein the detectable reporter is a luminescent or fluorescent protein.

10. The method of claim 9, wherein the fluorescent protein is selected from the group consisting of green fluorescent protein (GFP), enhanced green fluorescent protein (EGFP), yellow fluorescent protein, cyan fluorescent protein, blue fluorescent protein, red fluorescent protein, HcRed, and analogs thereof, or the luminescent protein is luciferase or an analog thereof.

11. The method of claim 9, wherein the transgenic mouse has progeny and the progeny of the mouse each have a genome comprising said nucleic acid construct.

12. The method of claim 9, wherein the predetermined chemical, behavioral, or pharmacological stimulus is administration of a drug, pain, or pleasure; induction of dendritic outgrowth; or learning.

13. The method of claim 12, wherein the learning is selected from the group consisting of an elevated plus maze, a light/dark box, an open field test, and a water maze.

14. The method of claim 9, wherein the predetermined chemical, behavioral, or pharmacological stimulus is selected from the group consisting of fear; sensory deprivation or stimulation; stress; reward for behavior that the mouse attends to; conditioning; visual, audio, location or olfactory cues; administration of a mind altering drug selected from the group consisting of nicotine, marijuana, cocaine, heroin, alcohol, and functional equivalents thereof; mating; aggression; sexual behavior, maternal behavior; social dominance; and deprivation of water or food.

15. The method of claim 14, wherein the location cue is linked to drug addiction.

16. The method of claim 15, wherein the drug is selected from the group consisting of nicotine, marijuana, caffeine, cocaine, heroin, and alcohol.

17. The method of claim 9, wherein the isolated cells comprise cells from the brain of the transgenic mouse.

18. The method of claim 9, wherein the isolated cells comprise at least a section or a slice of the brain of the transgenic mouse.

19. A method of identifying one or more living sensory neurons activated by a behavioral stimulus in a transgenic mouse, said method comprising:
(a) providing a transgenic mouse whose genome comprises a nucleic acid construct comprising the c-fos 5' untranslated region, which comprises one or more regulatory sequences and the complete genomic sequence of the c-fos gene fused in frame to a detectable reporter wherein the one or more regulatory sequences is activated in a sensory neuron in response to a predetermined behavioral stimulus,
(b) administering the predetermined behavioral stimulus to the transgenic mouse of step (a),
(c) identifying ex vivo in a brain slice derived from the transgenic mouse in step (b) one or more living sensory neurons expressing the detectable reporter, while maintaining the sensory neuron's viability, and wherein the detectable reporter is a luminescent or fluorescent protein.

20. The method of claim 19, wherein the fluorescent protein is selected from the group consisting of green fluorescent protein (GFP), enhanced green fluorescent protein (EGFP), yellow fluorescent protein, cyan fluorescent protein, blue fluorescent protein, red fluorescent protein, HcRed, and analogs thereof, or the luminescent protein is luciferase or an analog thereof.

21. The method of claim 19, wherein the transgenic mouse has progeny, and the progeny of the mouse each have a genome comprising said nucleic acid construct.

22. The method of claim 19, wherein the predetermined behavioral stimulus is selected from the group consisting of administration of pain, administration of pleasure, learning, fear, sensory deprivation, sensory stimulation, stress, reward for behavior the mouse attends to, conditioning, visual cues, audio cues, location cues, olfactory cues, mating, aggression, sexual behavior, maternal behavior, social dominance, deprivation of food, and deprivation of water.

23. The method of claim 22, wherein the learning is selected from the group consisting of an elevated plus maze, a light/dark box, an open field test, and a water maze.

24. The method of claim 22, wherein the location cue is linked to drug addiction.

25. The method of claim 24, wherein the drug is selected from the group consisting of nicotine, marijuana, caffeine, cocaine, heroin and alcohol.

26. A method of identifying one or more living sensory neurons activated by a behavioral stimulus in a population of isolated sensory neurons, said method comprising:
(a) providing a transgenic mouse whose genome comprises a nucleic acid construct comprising the c-fos 5' untranslated region, which comprises one or more regulatory sequences and the complete genomic sequence of the c-fos gene fused in frame to a detectable reporter wherein the one or more regulatory sequences is activated in a sensory neuron in response to a predetermined behavioral stimulus,
(b) administering the predetermined behavioral stimulus to the transgenic mouse of step (a),
(c) isolating a population of sensory neurons from the brain of the transgenic mouse in step (b), while maintaining the sensory neuron's viability, and
(d) identifying a living sensory neuron expressing the detectable reporter in a population of living sensory neurons, wherein the detectable reporter is a luminescent or fluorescent protein.

27. The method of claim 26, wherein the fluorescent protein is selected from the group consisting of green fluorescent protein (GFP), enhanced green fluorescent protein (EGFP), yellow fluorescent protein, cyan fluorescent protein, blue fluorescent protein, red fluorescent protein, HcRed, and analogs thereof, or the luminescent protein is luciferase or an analog thereof.

28. The method of claim 26, wherein the transgenic mouse has progeny, and the progeny of the mouse each have a genome comprising said nucleic acid construct.

29. The method of claim 26, wherein the predetermined behavioral stimulus is selected from the group consisting of administration of pain, administration of pleasure, learning, fear, sensory deprivation, sensory stimulation, stress, reward for behavior the mouse attends to, conditioning, visual cues, audio cues, location cues, olfactory cues, mating, aggression, sexual behavior, maternal behavior, social dominance, deprivation of food, and deprivation of water.

30. The method of claim 29, wherein the learning is selected from the group consisting of an elevated plus maze, a light/dark box, an open field test, and a water maze.

31. The method of claim 29, wherein the location cue is linked to drug addiction.

32. The method of claim 31, wherein the drug is selected from the group consisting of nicotine, marijuana, caffeine, cocaine, heroin and alcohol.

33. The method of claim 26, wherein the isolated cells comprise cells from the brain of the transgenic mouse.

34. The method of claim 26, wherein the isolated cells comprise at least a section or a slice of the brain of the transgenic mouse.

* * * * *

UNITED STATES PATENT AND TRADEMARK OFFICE
CERTIFICATE OF CORRECTION

PATENT NO. : 8,952,213 B2  
APPLICATION NO. : 10/424164  
DATED : February 10, 2015  
INVENTOR(S) : Alison L. Barth Page 1 of 1

It is certified that error appears in the above-identified patent and that said Letters Patent is hereby corrected as shown below:

On the title page, line (73) the following Assignee information should be deleted:

"The Board of Trustees of the Leland Stanford Junior
University, Pittsburgh, PA (US)"

On the title page, line (73) the following Assignee information should be inserted:

-- The Board of Trustees of the Leland Stanford Junior
University, Palo Alto, CA (US)

Carnegie Mellon University,
Pittsburgh, PA (US) --

Signed and Sealed this
Thirteenth Day of October, 2015

Michelle K. Lee
*Director of the United States Patent and Trademark Office*